(12) United States Patent
Liu et al.

(10) Patent No.: US 7,598,350 B2
(45) Date of Patent: Oct. 6, 2009

(54) HUMAN ANTI-EPIDERMAL GROWTH FACTOR RECEPTOR ANTIBODY

(75) Inventors: Meilin Liu, Brooklyn, NY (US); Zhenping Zhu, Oakland, NJ (US)

(73) Assignee: ImClone LLC, New York, NY (US)

(*) Notice: Subject to any disclaimer, the term of this patent is extended or adjusted under 35 U.S.C. 154(b) by 0 days.

(21) Appl. No.: 10/593,804

(22) PCT Filed: Mar. 21, 2005

(86) PCT No.: PCT/US2005/009583

§ 371 (c)(1), (2), (4) Date: Mar. 13, 2007

(87) PCT Pub. No.: WO2005/090407

PCT Pub. Date: Sep. 29, 2005

(65) Prior Publication Data

US 2007/0264253 A1    Nov. 15, 2007

Related U.S. Application Data

(60) Provisional application No. 60/554,555, filed on Mar. 19, 2004, provisional application No. 60/624,264, filed on Nov. 2, 2004.

(51) Int. Cl.
C07K 16/28    (2006.01)

(52) U.S. Cl. .................................. 530/387.9

(58) Field of Classification Search ............... None
See application file for complete search history.

(56) References Cited

U.S. PATENT DOCUMENTS

| | | |
|---|---|---|
| 4,186,567 A | 2/1980 | Monden et al. |
| 4,510,924 A | 4/1985 | Gray |
| 4,763,642 A | 8/1988 | Horowitz |
| 4,816,397 A | 3/1989 | Boss et al. |
| 4,816,401 A | 3/1989 | Taupier et al. |
| 4,816,567 A | 3/1989 | Cabilly et al. |
| 4,846,782 A | 7/1989 | Bonnem |
| 4,863,902 A | 9/1989 | Amagase et al. |
| 4,943,533 A | 7/1990 | Mendelsohn et al. |
| 4,946,778 A | 8/1990 | Ladner et al. |
| 5,196,446 A | 3/1993 | Levitzki et al. |
| 5,225,539 A | 7/1993 | Winter et al. |
| 5,260,203 A | 11/1993 | Ladner et al. |
| 5,455,030 A | 10/1995 | Ladner et al. |
| 5,468,754 A | 11/1995 | Hausheer et al. |
| 5,470,571 A | 11/1995 | Herlyn et al. |
| 5,518,889 A | 5/1996 | Ladner et al. |
| 5,545,807 A | 8/1996 | Surani et al. |
| 5,550,114 A | 8/1996 | Strayer |
| 5,558,864 A | 9/1996 | Bendig et al. |
| 5,559,235 A | 9/1996 | Luzzio et al. |
| 5,565,332 A | 10/1996 | Hoogenboom et al. |
| 5,604,233 A | 2/1997 | Hausheer et al. |
| 5,616,582 A | 4/1997 | Barker et al. |
| 5,646,153 A | 7/1997 | Spada et al. |
| 5,656,655 A | 8/1997 | Spada et al. |
| 5,658,570 A | 8/1997 | Newman et al. |
| 5,663,144 A | 9/1997 | Greene et al. |
| 5,677,171 A | 10/1997 | Hudziak et al. |
| 5,679,683 A | 10/1997 | Bridges et al. |
| 5,693,780 A | 12/1997 | Newman et al. |
| 5,705,157 A | 1/1998 | Greene |
| 5,707,632 A | 1/1998 | Williams et al. |
| 5,736,534 A | 4/1998 | Arnold |
| 5,770,195 A | 6/1998 | Hudziak et al. |
| 5,770,599 A | 6/1998 | Gibson et al. |
| 5,789,427 A | 8/1998 | Chen et al. |
| 5,837,242 A | 11/1998 | Holliger et al. |
| 5,840,301 A | 11/1998 | Rockwell et al. |
| 5,844,093 A | 12/1998 | Kettleborough et al. |
| 5,846,565 A | 12/1998 | Brem et al. |
| 5,851,999 A | 12/1998 | Ullrich et al. |
| 5,855,885 A | 1/1999 | Smith et al. |
| 5,859,205 A | 1/1999 | Adair et al. |
| 5,861,499 A | 1/1999 | Rockwell et al. |

(Continued)

FOREIGN PATENT DOCUMENTS

| | | | |
|---|---|---|---|
| WO | WO/98/50433 | * | 5/1998 |
| WO | WO/03/064606 | * | 8/2003 |
| WO | WO/2004/005890 | * | 1/2004 |

OTHER PUBLICATIONS

Janeway et al. eds., chapter 3, Immunobiology, chapter 3, Garland publishing, New York, 2001, ISBN 081533642 X.*
Rudikoff et al., Single amino acid substitution altering antigen-binding specificit. Proc. Natl. Acad. Sci. USA, 79, 1979-1983, 1982.*
Kobrin et al., A V Region Mutation in a Phosphocholine-Binding Monoclonal Antibody Results in Loss of Antigen Binding, J. Immunol., 146, 2017-2020, 1991.*
Barrios et al., Length of the antibody heavy chain complementarity determining region 3 as aspecificity-determining factor. J. Mol. Recog., 17, 332-338, 2004.*
Sliwkowski et al., Journal of Biological Chemistry 269:14661-5 (1994).

(Continued)

*Primary Examiner*—Lorraine Spector
*Assistant Examiner*—Elly-Gerald Stoica
(74) *Attorney, Agent, or Firm*—Gregory A. Cox

(57) ABSTRACT

The present invention provides a fully human antibody that binds human EGFR with affinity comparable to or higher than IMC-C225, and that neutralizes activation of EGFR. Antibodies include whole immunoglobulins, monovalent Fabs and single chain antibodies, multivalent single chains antibodies, diabodies, triabodies, and single domain antibodies. The invention further provides nucleic acids and host cells and animals that encode and express these antibodies. The invention further provides a method for neutralizing activation of EGFR, treating in a mammal with neoplastic growth and non-cancerous hyperproliferative diseases using the antibodies alone or in combination with other agents.

4 Claims, 15 Drawing Sheets

U.S. PATENT DOCUMENTS

| | | | |
|---|---|---|---|
| 5,866,363 | A | 2/1999 | Pieczenik |
| 5,866,572 | A | 2/1999 | Barker et al. |
| 5,869,465 | A | 2/1999 | Morgan, Jr. et al. |
| 5,880,133 | A | 3/1999 | Hausheer et al. |
| 5,885,793 | A | 3/1999 | Griffiths et al. |
| 5,886,363 | A | 3/1999 | Hamada et al. |
| 5,891,996 | A | 4/1999 | Mateo de Acosta del Rio et al. |
| 5,914,269 | A | 6/1999 | Bennett et al. |
| 5,925,566 | A | 7/1999 | Davis et al. |
| 5,942,602 | A | 8/1999 | Wels et al. |
| 5,955,311 | A | 9/1999 | Rockwell et al. |
| 5,969,108 | A | 10/1999 | McCafferty et al. |
| 6,004,967 | A | 12/1999 | McMahon et al. |
| 6,129,915 | A | 10/2000 | Wels et al. |
| 6,140,317 | A | 10/2000 | Traxler et al. |
| 6,217,866 | B1 | 4/2001 | Schlessinger et al. |
| 6,235,883 | B1 * | 5/2001 | Jakobovits et al. ..... 530/388.22 |
| 6,265,411 | B1 | 7/2001 | Thomas et al. |
| 6,417,168 | B1 | 7/2002 | Greene et al. |
| 6,506,883 | B2 | 1/2003 | Meteo de Acosta del Rio et al. |
| 6,605,448 | B1 | 8/2003 | Pieczenik |
| 6,632,927 | B2 | 10/2003 | Adair et al. |
| 6,639,055 | B1 | 10/2003 | Carter et al. |
| 6,685,940 | B2 | 2/2004 | Andya et al. |
| 6,699,473 | B2 | 3/2004 | Raisch et al. |
| 2003/0105057 | A1 | 6/2003 | Fu et al. |
| 2003/0157104 | A1 | 8/2003 | Waksal |
| 2003/0194403 | A1 | 10/2003 | van de Winkel et al. |
| 2004/0022785 | A1 | 2/2004 | Clinton et al. |
| 2004/0057950 | A1 | 3/2004 | Waksal et al. |
| 2004/0116330 | A1 | 6/2004 | Naito et al. |
| 2005/0112120 | A1 | 5/2005 | Waksal |
| 2005/0148607 | A1 | 7/2005 | Suzuki et al. |
| 2005/0176633 | A1 | 8/2005 | Ullrich et al. |
| 2005/0220786 | A1 | 10/2005 | Mahler et al. |
| 2005/0281814 | A1 | 12/2005 | Buchsbaum |

OTHER PUBLICATIONS

Snider et al., Ann Thorac Surg 62:1454 (1996).
Stanton et al., Br. J. Cancer 70(3):427-33 Abstract Only (1994).
Tzahar et al., The EMBO Journal 16:4938-50 (1997).
Van Gog et al., Int. J. Cancer 77:13 (1998).
Visakorpi et al., Mod. Pathol. 5(6):643-8 (1992).
Walter et al., PNAS 77:5197-5200 (1980).
Wazer et al., Br. J. Radiology 62:1079-83 (1989).
Witters et al., Breast Cancer Research Treatment 42:1 (1997).
Wollman et al., Int. J. Radiat. Oncol. Biol. Phys. 30(1):91-98 (1994).
Yang et al., PNAS 85:1189-93 (1988).
Zaks, et al., Cancer Research 58:4902-8 (1998).
Zhang & Hung, Oncogene 12:571-75 (1996).

* cited by examiner

FIG. 1
Cloning Vectors for Immunoglobulin Gene Expression
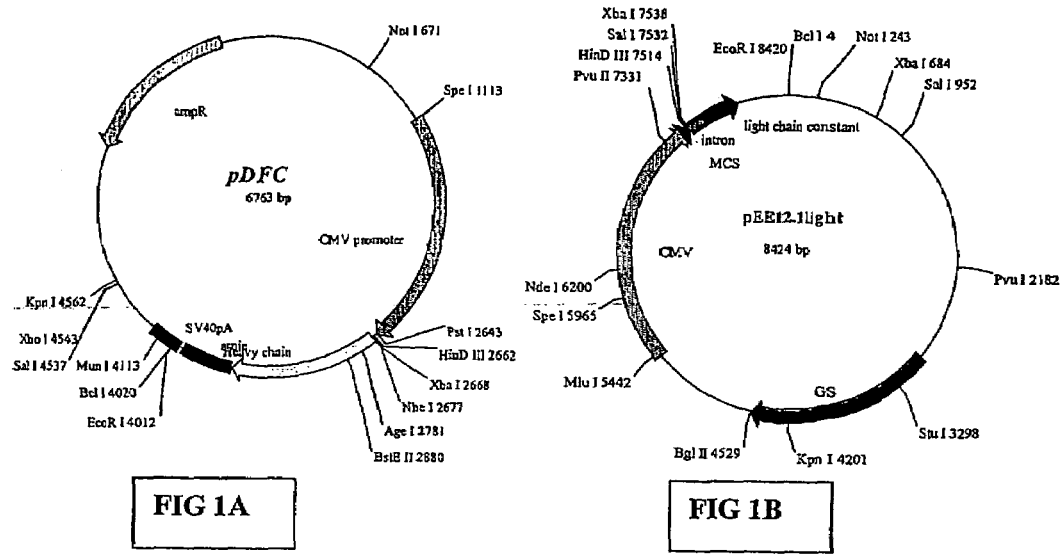
FIG 1A
FIG 1B
pGS-11F8
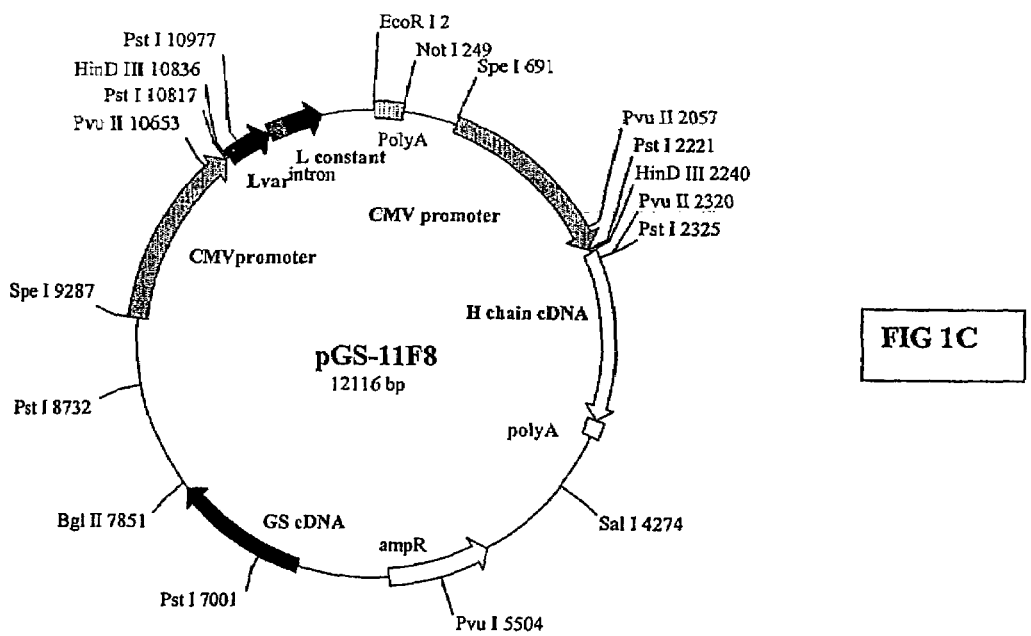
FIG 1C Restriction Digest Profile of pGS-11F8

FIG. 7
Inhibition of EGFR Phosphorylation in A431
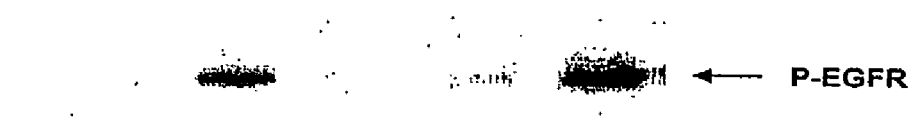
FIG. 7A
FIG. 7B

PBS　　　　　　　　IMC-11F8

A   B

C   D

E   F

A

B

C

D

HUMAN ANTI-EPIDERMAL GROWTH FACTOR RECEPTOR ANTIBODY

The application is a 371 PCT/US05/09583 filed Mar. 21, 2005 which claims benefit of 60/544,555 filed Mar. 19, 2004 and claims benefit of 60/624,624 filed Nov. 02, 2004.

FIELD OF THE INVENTION

The present invention is directed to monoclonal antibodies that are specific the epidermal growth factor receptor (EGFR). These antibodies can be used in treating neoplastic diseases and hyperproliferative disorders, among others.

BACKGROUND OF THE INVENTION

Although normal cells proliferate by the highly controlled activation of growth factor receptor tyrosine kinases (RTKs) by their respective ligands, cancer cells also proliferate by the activation of growth factor receptors, but lose the careful control of normal proliferation. The loss of control may be caused by numerous factors, such as the overexpression of growth factors and/or receptors, and autonomous activation of biochemical pathways regulated by growth factors. Some examples of RTKs involved in tumorigenesis are the receptors for epidermal growth factor (EGFR), platelet-derived growth factor (PDGFR), insulin-like growth factor (IGFR), nerve growth factor (NGFR), and fibroblast growth factor (FGF). Binding of these growth factors to their cell surface receptors induces receptor activation, which initiates and modifies signal transduction pathways and leads to cell proliferation and differentiation.

Members of the epidermal growth factor (EGF) receptor family are particularly important growth factor receptor tyrosine kinases associated with tumorigenesis of epidermal cells. The first member of the EGF receptor family to be discovered was EGFR, which is expressed on many types of tumor cells. EGFR has been found to be involved in regulation of tumor cell division and growth, repair and survival, angiogenesis, invasion and tumor metastasis.

EGFR is a 170 kD membrane-spanning glycoprotein with an extracellular ligand binding domain, a transmembrane region and a cytoplasmic protein tyrosine kinase domain. Examples of ligands that stimulate EGFR include epidermal growth factor (EGF), transforming growth factor-α (TGF-α), heparin-binding growth factor (HBGF), β-cellulin, and Cripto-1. Binding of specific ligands results in EGFR autophosphorylation, activation of the receptor's cytoplasmic tyrosine kinase domain and initiation of multiple signal transduction pathways that regulate tumor growth and survival. The EGFR pathway also influences production of various other angiogenic factors, such as VEGF and basis fibroblastic growth factor (bFGF), in tumors.

Growth factors that activate EGFR are also thought to play a role in tumor angiogenesis. Angiogenesis, which refers to the formation of capillaries from pre-existing vessels in the embryo and adult organism, is known to be a key element in tumor growth, survival and metastasis. It has been reported that EGFR mediated stimulation of tumor cells leads to increased expression of the angiogenic factors vascular endothelial growth factor (VEGF), interleukin-8 (IL-8), and basic fibroblast growth factor (bFGF), which can lead to activation of tumor-associated vascular endothelial cells. Stimulation of tumor-associated vascular endothelial cells may also occur through activation of their own EGF receptors, by tumor produced growth factors such as TGF-α and EGF.

It has been reported that many human tumors express or overexpress EGFR. Expression of EGFR is correlated with poor prognosis, decreased survival, and/or increased metastasis. EGFR, because of this involvement in tumorigenesis, has been specifically targeted for anticancer therapies. These therapies have predominantly included either a monoclonal antibody that blocks binding of ligand to the extracellular domain of the receptor or a synthetic tyrosine kinase inhibitor that acts directly on the intracellular region to prevent signal transduction.

For example, Cetuximab MAb (ERBITUX®) is a recombinant, human/mouse chimeric, monoclonal antibody that binds specifically to the extracellular domain of the human EGFR. Cetuximab is an EGFR antagonist, which blocks ligand binding to EGFR, prevents receptor activation, and inhibits growth of tumor cells that express EGFR. Cetuximab has been approved for use in combination with or without irinotecan in the treatment of patients with epidermal growth factor receptor-expressing, metastatic colorectal cancer who are refractory or can not tolerate irinotecan-based chemotherapy. Cetuximab has also been shown to be effective for treatment of psoriasis.

SUMMARY OF THE INVENTION

The present invention provides monoclonal antibodies or fragments thereof specific for EGFR, preferably the extracellular region of EGFR, comprising anywhere from one to six complementarity determining regions (CDRs) selected from the group consisting of SEQ ID NO:2, SEQ ID NO:4, SEQ ID NO:6, SEQ ID NO:10, SEQ ID NO:12, and SEQ ID NO:14. Preferably, the antibodies are human. More preferably, the antibodies of the present invention, or fragments thereof, comprise SEQ ID NO:2, SEQ ID NO:4, and SEQ ID NO:6. Alternatively, but also preferably, the antibodies of the present invention, or fragments thereof, comprise SEQ ID NO:10, SEQ ID NO:12, and SEQ ID NO:14. More preferably the antibodies of the present invention, or fragments thereof, comprise a heavy chain variable region of SEQ ID NO:8 and/or a light chain variable region of SEQ ID NO:16. Such antibodies or fragments thereof of the present invention have various properties, including the ability to neutralize EGFR and prevent binding of a ligand of EGFR to its receptor.

Additionally, the present invention provides isolated polynucleotides encoding the present antibodies or fragments thereof as well as expression vectors comprising these polynucleotide sequences operably linked to an expression sequence. Recombinant host cells comprising the expression vector, or a progeny thereof, wherein the cell expresses the present antibodies or fragments thereof are also provided. Methods are also provided for producing antibodies or fragments thereof comprising culturing these cells under conditions permitting expression of the antibodies or fragments thereof The antibodies or fragments thereof can then be purified from the cell or medium of the cell.

Also, the present invention provides methods of treating tumor growth in a mammal, comprising administering to the mammal an effective amount of a present antibody. The present antibodies can be coadministered with antibodies that bind to other RTKs. The methods can also comprise administering to the mammal an anti-neoplastic agent or treatment, including, for example, a chemotherapeutic agent and/or radiation. In certain embodiments, tumor growth is inhibited. In preferred embodiments, treatment results in tumor regression.

The present invention also provides methods of treating a non-cancer hyperproliferative disease, e.g., psoriasis, in a mammal comprising administering to the mammal an effective amount of the present antibody.

BRIEF DESCRIPTION OF THE FIGURES

FIGS. 1A and 1B shows the cloning vectors for expression of immunoglobulin genes, pDFC and pEE12.1L. FIG. 1C shows the resulting single full human anti-EGFR antibody containing vector plasmid, pGS-11F8.

FIG. 7 shows Western Blot analysis of EGFR phosphorylation in the presence of unstimulated control cells (lane 1), EGF (lane 2), IMC-C225 (lane 3), IMC-11F8 (lane4) and control antibody (lane 5). FIG. 5A shows phosphorylated EGFR using an anti-phosphotyrosine antibody and FIG. 5B shows total EGFR in the stimulated cells.

FIG. 8A shows anti-phosphotyrosine antibody Western blot analysis of EGFR in unstimulated control cells (lane 1), stimulated cells treated with no IMC-11F8 antibody (lane 2), 15 µg/mL (lane 3), 3 µg/mL (lane 4), and 0.6 µ/mL (lane 3) IMC-11F8. FIG. 8B shows total EGFR.

DETAILED DESCRIPTION OF THE INVENTION

Figure 2:
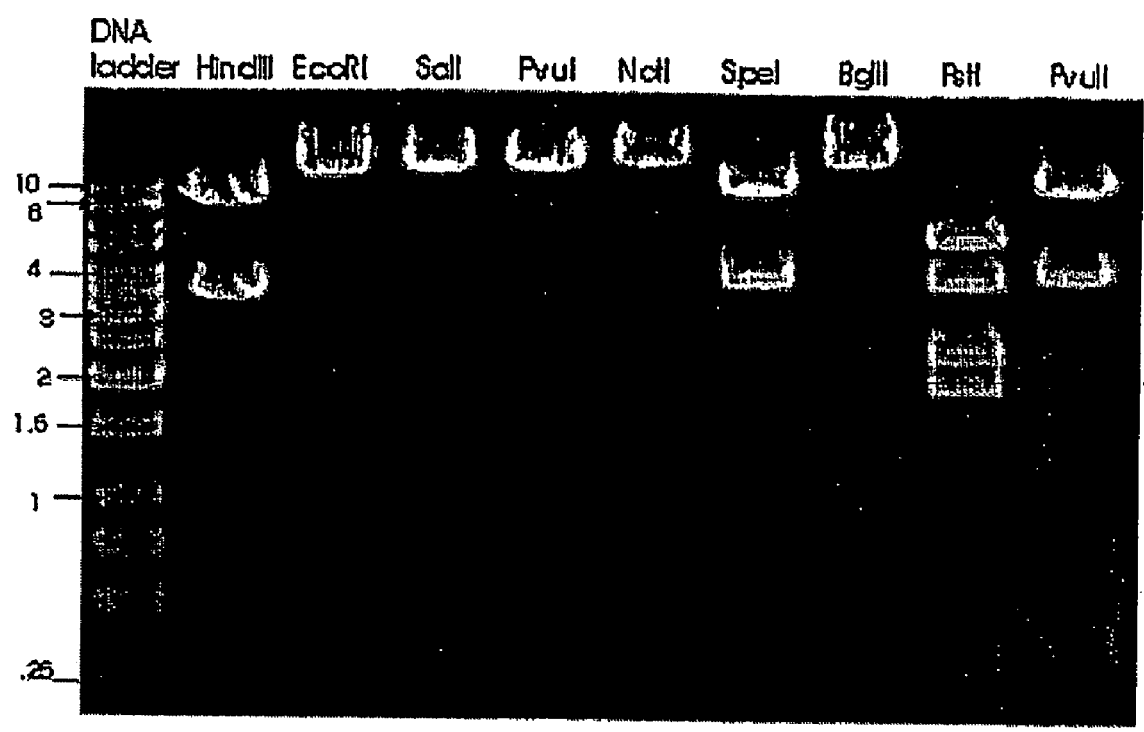
FIG. 2 shows the restriction digest profile of pGS-11F8. DNA size markers are indicated in the DNA ladder as kilobase pairs.

The present invention provides monoclonal antibodies and fragments thereof that are specific for EGFR, as well as isolated or purified polynucleotide sequences encoding the antibodies. Antibodies of the present invention are preferably human and can be used to treat neoplastic diseases, including solid and non-solid tumors and for treatment of hyperproliferative disorders.

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain ($V_L$) and/or one constant domain ($C_L$). The heavy chain can also comprise one variable domain ($V_H$) and/or, depending on the class or isotype of antibody, three or four constant domains ($C_H1$, $C_H2$, $C_H3$ and $C_H4$). In humans, the isotypes are IgA, IgD, IgE, IgG, and IgM, with IgA and IgG further subdivided into subclasses or subtypes ($IgA_{1-2}$ and $IgG_{1-4}$).

Generally, the variable domains show considerable amino acid sequence variability from one antibody to the next, particularly at the location of the antigen-binding site. Three regions, called hypervariable or complementarity-determining regions (CDRs), are found in each of $V_L$ and $V_H$, which are supported by less variable regions called framework variable regions.

The portion of an antibody consisting of $V_L$ and $V_H$ domains is designated Fv (fragment variable) and constitutes the antigen-binding site. Single chain Fv (scFv) is an antibody fragment containing a $V_L$ domain and a $V_H$ domain on one polypeptide chain, wherein the N terminus of one domain and the C terminus of the other domain are joined by a flexible linker (see, e.g., U.S. Pat. No. 4,946,778 (Ladner et al.); WO 88/09344, (Huston et al.). WO 92/01047 (McCafferty et al.) describes the display of scFv fragments on the surface of soluble recombinant genetic display packages, such as bacteriophage.

The peptide linkers used to produce the single chain antibodies can be flexible peptides selected to assure that the proper three-dimensional folding of the $V_L$ and $V_H$ domains occurs. The linker is generally 10 to 50 amino acid residues. Preferably, the linker is 10 to 30 amino acid residues. More preferably the linker is 12 to 30 amino acid residues. Most preferably is a linker of 15 to 25 amino acid residues. An example of such linker peptides includes (Gly-Gly-Gly-Gly-Ser)$_3$ (SEQ ID NO:19).

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater per mneability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one $V_H$ and one $V_L$ domain covalently linked by a first peptide linker, can be covalently linked by at least one or more peptide linker to form a multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of amino acid residues is about one hundred.

Two single chain antibodies can be combined to form a diabody, also known as a bivalent dimer. Diabodies have two chains and two binding sites, and can be monospecific or bispecific. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a $V_L$ or $V_H$ domain directly fused to the carboxyl terminus of a $V_L$ or $V_H$ domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Fab (Fragment, antigen binding) refers to the fragments of the antibody consisting of $V_L$, $C_L$, $V_H$ and $C_H1$ domains. Those generated following papain digestion simply are referred to as Fab and do not retain the heavy chain hinge region. Following pepsin digestion, various Fabs retaining the heavy chain hinge are generated. Those divalent fragments with the interchain disulfide bonds intact are referred to as $F(ab')_2$, while a monovalent Fab' results when the disulfide bonds are not retained. $F(ab')_2$ fragments have higher avidity for antigen that the monovalent Fab fragments.

Fc (Fragment crystallization) is the designation for the portion or fragment of an antibody that comprises paired heavy chain constant domains. In an IgG antibody, for example, the Fc comprises $C_{H2}$ and $C_{H3}$ domains. The Fc of an IgA or an IgM antibody further comprises a $C_{H4}$ domain. The Fc is associated with Fc receptor binding, activation of complement-mediated cytotoxicity and antibody-dependent cellular-cytoxicity (ADCC). For antibodies such as IgA and IgM, which are complexes of multiple IgG like proteins, complex formation requires Fc constant domains.

Finally, the hinge region separates the Fab and Fc portions of the antibody, providing for mobility of Fabs relative to each other and relative to Fc, as well as including multiple disulfide bonds for covalent linkage of the two heavy chains.

Thus, antibodies of the invention include, but are not limited to, naturally occurring antibodies, bivalent fragments such as $(Fab')_2$, monovalent fragments such as Fab, single chain antibodies, single chain Fv (scFv), single domain antibodies, multivalent single chain antibodies, diabodies, triabodies, and the like that bind specifically with antigens.

The antibodies, or fragments thereof, of the present invention are specific for EGFR. Antibody specificity refers to selective recognition of the antibody for a particular epitope of an antigen. Antibodies, or fragments thereof, of the present invention, for example, can be monospecific or bispecific. Bispecific antibodies (BsAbs) are antibodies that have two different antigen-binding specificities or sites. Where an antibody has more than one specificity, the recognized epitopes can be associated with a single antigen or with more than one antigen. Thus, the present invention provides bispecific antibodies, or fragments thereof, that bind to two different antigens, with at least one specificity for EGFR.

Specificity of the present antibodies, or fragments thereof, for EGFR can be determined based on affinity and/or avidity. Affinity, represented by the equilibrium constant for the dissociation of an antigen with an antibody ($K_d$), measures the binding strength between an antigenic determinant and an antibody-binding site. Avidity is the measure of the strength of binding between an antibody with its antigen. Avidity is related to both the affinity between an epitope with its antigen binding site on the antibody, and the valence of the antibody, which refers to the number of antigen binding sites of a particular epitope. Antibodies typically bind with a dissociation constant ($K_d$) of $10^{-5}$ to $10^{-11}$ liters/mol. Any $K_d$ less than $10^{-4}$ liters/mol is generally considered to indicate nonspecific binding. The lesser the value of the $K_d$, the stronger the binding strength between an antigenic determinant and the antibody binding site.

As used herein, "antibodies" and "antibody fragments" includes modifications that retain specificity for the EGF receptor. Such modifications include, but are not limited to, conjugation to an effector molecule such as a chemotherapeutic agent (e.g., cisplatin, taxol, doxorubicin) or cytotoxin (e.g., a protein, or a non-protein organic chemotherapeutic agent). The antibodies can be modified by conjugation to detectable reporter moieties. Also included are antibodies with alterations that affect non-binding characteristics such as half-life (e.g., pegylation).

Proteins and non-protein agents may be conjugated to the antibodies by methods that are known in the art. Conjugation methods include direct linkage, linkage via covalently attached linkers, and specific binding pair members (e.g., avidin-biotin). Such methods include, for example, that described by Greenfield et al., Cancer Research 50, 6600-6607 (1990) for the conjugation of doxorabicin and those described by Amon et al., Adv. Exp. Med. Biol. 303, 79-90 (1991) and by Kiseleva et al., Mol. Biol. (USSR) 25, 508-514 (1991) for the conjugation of platinum compounds.

Equivalents of the antibodies, or fragments thereof, of the present invention also include polypeptides with amino acid sequences substantially the same as the amino acid sequence of the variable or hypervariable regions of the full-length anti-EGFR antibodies disclosed herein. Substantially the same amino acid sequence is defined herein as a sequence with at least about 70%, preferably at least about 80%, and more preferably at least about 90% homology, as determined by the FASTA search method in accordance with Pearson and Lipman (Proc. Natl. Acad. Sci. USA 85, 2444-8 (1988)), including sequences that are at least about 70%, preferably at least about 80%, and more preferably at least about 90% identical.

Such antibodies will have the same or similar binding, ligand blocking, and receptor neutralizing activities to antibodies of the invention that comprise SEQ ID NOS:8 and 16, particularly where there are conservative amino acid substitutions. A conservative amino acid substitution is defined as a change in the amino acid composition by way of changing one or more amino acids of a peptide, polypeptide or protein, or fragment thereof The substitution is of amino acids with generally similar properties (e.g., acidic, basic, aromatic, size, positively or negatively charged, polarity, non-polarity) such that the substitutions do not substantially alter relevant peptide, polypeptide or protein characteristics (e.g., charge, isoelectric point, affinity, avidity, conformation, solubility) or activity. Typical conservative substitutions are selected within groups of amino acids, which groups include, but are not limited to:

(1) hydrophobic: methionine (M), alanine (A), valine (V), leucine (L), isoleucine (I);
(2) hydrophilic: cysteine (C), serine (S), threonine (T), asparagine (N), glutamine (Q);
(3) acidic: aspartic acid (D), glutamic acid (E);
(4) basic: histidine (H), lysine (K), arginine (R);
(5) aromatic: phenylalanine (F), tyrosine (Y) and tryptophan (W);
(6) residues that influence chain orientation: gly, pro.

Antibodies of the present invention further include those for which binding characteristics have been improved by direct mutation, methods of affinity maturation, phage display, or chain shuffling. Affinity and specificity can be modified or improved by mutating CDRs and screening for antigen binding sites having the desired characteristics (see, e.g., Yang et al., J. Mol. Biol., 254: 392-403 (1995)). CDRs are mutated in a variety of ways. One way is to randomize individual residues or combinations of residues so that in a population of, otherwise identical antigen binding sites, all twenty amino acids are found at particular positions. Alternatively, mutations are induced over a range of CDR residues by error prone PCR methods (see, e.g., Hawkins et al., J. Mol. Biol., 226: 889-896 (1992)). For example, phage display vectors containing heavy and light chain variable region genes can be propagated in mutator strains of E. coli (see, e.g., Low et al., J. Mol. Biol., 250: 359-368 (1996)). These methods of mutagenesis are illustrative of the many methods known to one of skill in the art.

Each domain of the antibodies of this invention can be a complete immunoglobulin domain (e.g., a heavy or light chain variable or constant domain), or it can be a functional equivalent or a mutant or derivative of a naturally-occurring domain, or a synthetic domain constructed, for example, in vitro using a technique such as one described in WO 93/11236 (Griffiths et al.). For instance, it is possible to join together domains corresponding to antibody variable domains, which are missing at least one amino acid. The important characterizing feature of the antibodies is the presence of an antigen binding site. The terms variable heavy and light chain fragment should not be construed to exclude variants that do not have a material effect on specificity.

The antibodies of the present invention, or fragments thereof, are human antibodies having one, two, three, four, five, and/or six complementarity determining regions (CDRs) selected from the group consisting of SEQ ID NO:2, SEQ ID NO:4, SEQ ID NO:6, SEQ ID NO:10, SEQ ID NO:12, and SEQ ID NO:14. Preferably, the antibodies (or fragments thereof) of the present invention have CDRs of SEQ ID NO:2, SEQ ID NO:4 and SEQ ID NO:6. Alternatively and also preferably, the present antibodies, or fragments thereof, have CDRs of SEQ ID NO:10, SEQ ID NO:12 and SEQ ID NO:14. The amino acid sequences of the CDRs are set forth below in Table 1.

TABLE 1

| Heavy Chain | | |
|---|---|---|
| CDR1 | SGDYYWS | SEQ ID NO:2 |
| CDR2 | YIYYSGSTDYNPSLKS | SEQ ID NO:4 |
| CDR3 | VSIFGVGTFDY | SEQ ID NO:6 |
| Light Chain | | |
| CDR1 | RASQSVSSYLA | SEQ ID NO:10 |

TABLE 1-continued

| CDR2 | DASNRAT | SEQ ID NO:12 |
|---|---|---|
| CDR3 | HQYGSTPLT | SEQ ID NO:14 |

In another embodiment, the present antibodies, or fragments thereof, can have a heavy chain variable region of SEQ ID NO:8 and/or a light chain variable region of SEQ ID NO:16. IMC-11F8 is a particularly preferred antibody of the present invention. This antibody has human $V_H$ and $V_L$ framework regions (FWs) as well as CDRs. The $V_H$ variable domain of IMC-11F8 (SEQ ID NO:8) has three CDRs (SEQ ID NOS:2, 4, and 6) and four FWs and the $V_L$ domain (SEQ ID NO:16) has three CDRs (SEQ ID NOS:10, 12, and 14) and four FWs.

Preferably, the antibodies, or fragments thereof, of the present invention neutralize EGFR. Binding of a ligand, e.g., EGF or TGF-α, to an external, extracellular domain of EGFR stimulates receptor dimerization, autophosphorylation of EGFR, activation of the receptor's internal, cytoplasmic tyrosine kinase domain, and initiation of multiple signal transduction and transactivation pathways involved in regulation of DNA synthesis (gene activation) and cell cycle progression or division. Also preferably, the anti-EGFR antibodies (or fragments thereof) of the present invention are specific for the extracellular region of EGFR. The present antibodies, or fragments thereof, further preferably prevent binding of a ligand of EGFR to its receptor. In this embodiment, the antibodies of the present invention, or fragments thereof, bind EGFR at least as strongly as the natural ligands of EGFR (EGF and TGF-α).

Neutralization of EGFR includes inhibition, diminution, inactivation and/or disruption of one or more of these activities normally associated with signal transduction. Thus, neutralizing EGFR has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

One measure of EGFR neutralization is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies in the context of the present invention. Phosphorylation can be detected, for example, using an antibody specific for phosphotyrosine in an ELISA assay or on a western blot. Some assays for tyrosine kinase activity are described in Panek et al., J. Pharmacol. Exp. Thera. 283: 1433-44 (1997) and Batley et al., Life Sci. 62: 143-50 (1998).

In addition, methods for detection of protein expression can be utilized to determine EGFR neutralization, wherein the proteins or protein activities or activation states being measured are regulated by EGFR tyrosine kinase activity. These methods include irnmunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., Cancer, 78:1284-92 (1996); Shimizu et al., Japan J. Cancer Res., 85:567-71(1994); Sauter et al., Am. J. Path., 148:1047-53 (1996); Collns, Glia, 15:289-

96 (1995); Radinsky et al., Clin. Cancer Res., 1:19-31 (1995); Petrides et al., Cancer Res., 50:3934-39 (1990); Hoffmann et al., Anticancer Res., 17:4419-26 (1997); Wikstrand et al., Cancer Res., 55:3140-48 (1995).

In vivo assays can also be utilized to determine EGFR neutralization. For example, receptor tyrosine kinase inhibition can be observed by mitogenic assays using cell lines stimulated with receptor ligand in the presence and absence of inhibitor. For example, A431 cells (American Type Culture Collection (ATCC), Rockville, Md.) stimulated with EGF can be used to assay EGFR inhibition. Another method involves testing for inhibition of growth of EGFR-expressing tumor cells, using for example, human tumor cells injected into a mouse. See, e.g., U.S. Pat. No. 6,365,157 (Rockwell et al.).

The present invention is not limited by any particular mechanism of EGPR neutralization. The anti-EGFR antibodies of the present invention can bind externally to the EGF cell surface receptor, block binding of ligand (e.g., EGF or TGF-α) and subsequent signal transduction mediated via the receptor-associated tyrosine kinase, and prevent phosphorylation of the EGFR and other downstream proteins in the signal transduction cascade. The receptor-antibody complex can also be internalized and degraded, resulting in receptor cell surface downregulation. Matrix metalloproteinases, which function in tumor cell invasion and metastasis, can also be downregulated by the antibodies of the present invention. Moreover, antibodies of the present invention may exhibit inhibition of growth factor production and angiogenesis.

Antibody fragments can be produced by cleaving a whole antibody, or by expressing DNA that encodes the fragment. Fragments of antibodies may be prepared by methods described by Lamoyi et al., *J. Immunol. Methods*, 56: 235-243 (1983) and by Parham, *J. Inimunol.* 131: 2895-2902 (1983). Such fragments may contain one or both Fab fragments or the F(ab')$_2$ fragment. Such fragments may also contain single-chain fragment variable region antibodies, i.e. scFv, dibodies, or other antibody fragments. Methods of producing such functional equivalents are disclosed in PCT Application WO 93/21319, European Patent Application No. EP 239400; PCT Application WO 89/09622; European Patent Application EP 338745; and European Patent Application EP 332424.

Preferred host cells for transformation of vectors and expression of the receptor antagonists of the present invention are mammalian cells, e.g., COS-7 cells, Chinese hamster ovary (CHO) cells, and cell lines of lymphoid origin such as lymphoma, myeloma (e.g. NS0), or hybridoma cells. Other eukaryotic hosts, such as yeasts, can be alternatively used.

Where it is desired to express a gene construct in yeast, a suitable selection gene for use in yeast is the trp1 gene present in the yeast plasmid YRp7. Stinchcomb et al. *Nature,* 282: 39 (1979); Kingsman et al., *Gene,* 7: 141 (1979). The trp1 gene provides a selection marker for a mutant strain of yeast lacking the ability to grow in tryptophan, for example, ATCC No.44076 or PEP4-1. Jones, *Genetics,* 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

The transformed host cells are cultured by methods known in the art in a liquid medium containing assimilable sources of carbon (carbohydrates such as glucose or lactose), nitrogen (amino acids, peptides, proteins or their degradation products such as peptones, ammonium salts or the like), and inorganic salts (sulfates, phosphates and/or carbonates of sodium, potassium, magnesium and calcium). The medium furthermore contains, for example, growth-promoting substances, such as trace elements, for example iron, zinc, manganese and the like.

As described in the examples below, high affinity anti-EGFR antibodies according to the present invention can be isolated from a phage display library constructed from human heavy chain and light chain variable region genes. For example, a variable domain of the invention can be obtained from a peripheral blood lymphocyte that contains a rearranged variable region gene. Alternatively, variable domain portions, such as CDR and FW regions, can be obtained from different human sequences. Over 90% of recovered clones after three rounds of selection are specific to EGFR. The binding affinities for EGFR of the screened Fabs are in the nM range, which are as high as those of several bivalent anti-EGFR monoclonal antibodies produced using hybridoma technology.

Antibodies and antibody fragments of the present invention can be obtained, for example, from naturally occurring antibodies, or Fab or scFv phage display libraries. It is understood that, to make a single domain antibody from an antibody comprising a $V_H$ and a $V_L$ domain, certain amino acid substitutions outside the CDRs can be desired to enhance binding, expression or solubility. For example, it can be desirable to modify amino acid residues that would otherwise be buried in the $V_H$-$V_L$ interface.

Further, antibodies and antibody fragments of the invention can be obtained by standard hybridoma technology (Harlow & Lane, ed., Antibodies: A Laboratory Manual, Cold Spring Harbor, 211-213 (1998), which is incorporated by reference herein) using transgenic mice (e.g., KM mice from Medarex, San Jose, Calif.) that produce human immunoglobulin gamma heavy and kappa light chains. In a preferred embodiment, a substantial portion of the human antibody producing genome is inserted into the genome of the mouse, and is rendered deficient in the production of endogenous murine antibodies. Such mice may be immunized subcutaneously (s.c.) with KDR (VEGFR-2) in complete Freund's adjuvant.

The protein used to identify EGFR binding antibodies of the invention is preferably EGFR and, more preferably, is the extracellular domain of EGFR. The EGFR extracellular domain can be free or conjugated to another molecule.

The present invention also provides isolated polynucleotides encoding the antibodies, or fragments thereof, described previously. The invention includes nucleic acids having a sequence encoding one, two, three, four, five and/or all six CDRs. Table 2 sets forth the nucleic acid sequences.

TABLE 2

Heavy Chain

CDR1 agtggtgatt actactggag t                              SEQ ID NO:1

CDR2 tacatctatt acagtgggag caccgactac SEQ ID NO:3
     aacccgtccc tcaaagt

CDR3 gtgtcgattt ttggagtggg ggacatttga SEQ IS NO:5
     ctac

Light Chain

CDR1 agggccagtc agagtgttag cagctactta SEQ ID NO:9
     gcc

CDR2 gatgcatcca acagggccac t                              SEQ ID NO:11

CDR3 caccagtatg gtagcacacc tctcact                        SEQ ID NO:13

DNA encoding human antibodies can be prepared by recombining DNA encoding human constant regions and variable regions, other than the CDRs, derived substantially or exclusively from the corresponding human antibody regions and DNA encoding CDRs derived from a human (SEQ ID NOS:1, 3, and 5 for the heavy chain variable domain CDRs and SEQ ID NOS:9, 11, and 13 for the light chain variable domain CDRs).

Suitable sources of DNAs that encode fragments of antibodies include any cell, such as hybridomas and spleen cells, that express the full-length antibody. The fragments may be used by themselves as antibody equivalents, or may be recombined into equivalents, as described above. The DNA deletions and recombinations described in this section may be carried out by known methods, such as those described in the publications listed above with regard to equivalents of antibodies and/or other standard recombinant DNA techniques, such as those described below. Another source of DNAs are single chain antibodies produced from a phage , display library, as is known in the art.

Additionally, the present invention provides expression vectors containing the polynucleotide sequences previously described operably linked to an expression sequence, a promoter and an enhancer sequence. A variety of expression vectors for the efficient synthesis of antibody polypeptide in prokaryotic, such as bacteria and eukaryotic systems, including but not limited to yeast and mammalian cell culture systems have been developed. The vectors of the present invention can comprise segments of chromosomal, non-chromosomal and synthetic DNA sequences.

Any suitable expression vector can be used. For example, prokaryotic cloning vectors include plasmids from *E. coli*, such as colE1, pCR1, pBR322, pMB9, pUC, pKSM, and RP4. Prokaryotic vectors also include derivatives of phage DNA such as *M*13 and other filamentous single-stranded DNA phages. An example of a vector useful in yeast is the 2 µ plasmid. Suitable vectors for expression in mammalian cues include well-known derivatives of SV40, adenovirus, retrovirus-derived DNA sequences and shuttle vectors derived from combination of functional mammalian vectors, such as those described above, and fu nctional plasmids and phage DNA.

Additional eukaryotic expression vectors are known in the art (e.g., P. J. Southern and P. Berg, J. Mol. Appl. Genet., 1, 327-341 (1982); Subramani et al., Mol. Cell. Biol., 1: 854-864 (1981); Kaufmann and Sharp, "Amplification And Expression of Sequences Cotransfected with a Modular Dihydrofolate Reductase Complementary DNA Gene," J. Mol. Biol. 159, 601-621 (1982); Kaufmann and Sharp, Mol. Cell. Biol. 159, 601-664 (1982); Scahill et al., "Expression And Characterization Of The Product Of A Human Immune Interferon DNA Gene In Chinese Hamster Ovary Cells," Proc. Nat'l Acad. Sci. USA 80, 4654-4659 (1983); Urlaub and Chasin, Proc. Nat'l Acad. Sci. USA 77, 4216-4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the try system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The present invention also provides recombinant host cells containing the expression vectors previously described. Antibodies of the present invention can be expressed in cell lines other than in hybridomas. Nucleic acids, which comprise a sequence encoding a polypeptide according to the invention, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, Chinese Hamster Ovary (CHO) cells, Baby Hamster Kidney (BHK) cells and many others. Suitable additional eukaryotic cells include yeast and other fungi. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus*, such as *Bacillus subtilis*, and *Streptomyces*.

These present recombinant host cells can be used to produce an antibody, or fragment thereof, by culturing the cells under conditions permitting expression of the antibody or fragment thereof and purifying the antibody or fragment thereof from the host cell or medium surrounding the host cell. Targeting of the expressed antibody or fragment for secretion in the recombinant host cells can be facilitated by inserting a signal or secretory leader peptide-encoding sequence (see, Shokri et al., Appl Microbiol Biotechnol. 60(6):654-64 (2003), Nielsen et al., Prot. Eng. 10:1-6 (1997) and von Heinje et al., Nucl. Acids Res. 14:4683-4690 (1986)) at the 5' end of the antibody-encoding gene of interest. These secretory leader peptide elements can be derived from either prokaryotic or eukaryotic sequences. Accordingly suitably, secretory leader peptides are used, being amino acids joined to the N-terminal end of a polypeptide to direct movement of the polypeptide out of the host cell cytosol and secretion into the medium.

The antibodies of this invention can be fused to additional amino acid residues. Such amino acid residues can be a peptide tag, perhaps to facilitate isolation. Other amino acid residues for homing of the antibodies to specific organs or tissues are also contemplated.

In another embodiment, an antibody of the present invention is made by expressing a nucleic acid encoding the antibody in a transgenic animal, such that the antibody is expressed and can be recovered. For example, the antibody can be expressed in a tissue specific manner that facilitates recovery and purification. In one such embodiment, an antibody of the invention is expressed in the mammary gland for secretion during lactation. Transgenic animals, include but are not limited to mice, goat, and rabbit.

A method of treating tumor growth in a mammal by administering to the mammal an effective amount of an antibody as previously described is also provided by the present invention. Suitable tumors to be treated according to the present invention preferably express EGFR. While not intended to be bound to any particular mechanism, the diseases and conditions which can be treated or prevented by the present methods include, for example, those in which tumor growth or pathogenic angiogenesis is stimulated through a EGFR paracrine and/or autocrine loop. That is, EGFR expressing tumors are characteristically sensitive to EGF present in their environment, and can further produce and be stimulated by EGF and/or TGF-α in an autocrine stimulatory loop. Treatment of such tumors according to the invention includes partial or complete inhibition of tumor growth. Notably, in certain embodiments, inhibition further includes tumor regression.

EGFR expression has been observed in a variety of human tumors, both in vitro and in vivo, and the levels of EGFR expression vary widely with tumor type. EGFR is expressed at varying levels on the cell surface in a significant percentage of human tumors, such as colorectal, head and neck (squamous cell), pancreatic, lung, breast, and renal cell carcinomas, as well as glioblastoma. In certain tumor types, EGFR expression is very common (e.g., 35% to 70% of ovarian cancers and approximately 25% to 77% of colorectal cancers). High levels of EGFR expression can occur in correlation with production of receptor ligands (i.e., EGF and TGF-α). EGFR expression has also been correlated with increased resistance to certain chemotherapeutic agents and radiotherapy. EGFR expression may also serve as a prognostic factor in certain types of tumors, as it has be associated with reduced survival, poor prognosis, and/or increased risk of metastasis. Moreover, increased EGFR expression exists in multiple tumor types.

Tumors to be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued.

Tumors that can be treated with antibodies of the present invention include tumors that are not vascularized, or not yet substantially vascularized, as well as vascularized tumors. Examples of solid tumors, which can be accordingly treated, include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma.

In another aspect of the invention, the anti-EGFR antibodies inhibit tumor-associated angiogenesis. EGFR stimulation of vascular endothelium is associated with vascularization of tumors. Typically, vascular endothelium is stimulated in a paracrine fashion by, e.g., EGF and/or TGF-α from other sources (e.g., tumor cells).

Accordingly, the human anti-EGFR antibodies are effective for treating subjects with vascularized tumors or neoplasms or angiogenic diseases. Such tumors and neoplasms include, for example, malignant tumors and neoplasms, such as blastomas, carcinomas or sarcomas, and highly vascular tumors and neoplasms. Cancers that can be treated by the methods of the present invention include, for example, cancers of the brain, genitourinary tract, lymphatic system, stomach, renal, colon, larynx and lung and bone. Non-limiting examples further include epidermoid tumors, squamous tumors, such as head and neck tumors, colorectal tumors, prostate tumors, breast tumors, lung tumors, including lung adenocarcinoma and small cell and non-small cell lung tumors, pancreatic tumors, thyroid tumors, ovarian tumors, and liver tumors. The method is also used for treatment of vascularized skin cancers, including squamous cell carcinoma, basal cell carcinoma, and skin cancers that can be treated by suppressing the growth of malignant keratinocytes, such as human malignant keratinocytes. Other cancers that can be treated include Kaposi's sarcoma, CNS neoplasms (neuroblastomas, capillary hemangioblastomas, meningiomas and cerebral metastases), melanoma, gastrointestinal and renal carcinomas and sarcomas, rhabdomyosarcoma, glioblastoma, including glioblastoma multiforme, and leiomyosarcoma.

The present invention also provides a method of treating a non-cancer hyperproliferative disease in a mammal comprising administering to the mammal an effective amount of the antibody of the present invention. As disclosed herein, "hyperproliferative disease" is defined as a condition caused by excessive growth of non-cancer cells that express a member of the EGFR family of receptors. The excess cells generated by a hyperproliferative disease express EGFR at normal levels or they may overexpress EGFR.

The types of hyperproliferative diseases that can be treated in accordance with the invention are any hyperproliferative diseases that are stimulated by a ligand of EGFR or mutants of such ligands. Examples of hyperproliferative disease include psoriasis, actinic keratoses, and seborrheic keratoses, warts, keloid scars, and eczema. Also included are hyperproliferative diseases caused by virus infections, such as papilloma virus infection. For example, psoriasis comes in many different variations and degrees of severity. Different types of psoriasis display characteristics such as pus-like blisters (pustular psoriasis), severe sloughing of the skin (erythrodermic psoriasis), drop-like dots (guttae psoriasis) and smooth inflamed lesions (inverse psoriasis). The treatment of all types of psoriasis (e. g., psoriasis vulgaris, psoriasis pustulosa, psoriasis erythrodermica, psoriasis arthropathica, parapsoriasis, palnoplantar pustulosis) is contemplated by the invention.

In the methods of the present invention, a therapeutically effective amount of an antibody of the invention is administered to a mammal in need thereof The term administering as used herein means delivering the antibodies of the present invention to a mammal by any method that can achieve the result sought. They can be administered, for example, intravenously or intramuscularly. Although human antibodies of the invention are particularly useful for administration to humans, they can be administered to other mammals as well. The tern mammal as used herein is intended to include, but is not limited to, humans, laboratory animals, domestic pets and far animals. Therapeutically effective amount means an amount of antibody of the present invention that, when administered to a mammal, is effective in producing the desired therapeutic effect, such as inhibiting kinase activity or inhibition of tumor growth.

The identification of such disease is well within the ability and knowledge of one skilled in the art. For example, human individuals who are either suffering from a clinically significant neoplastic or angiogenic disease or who are at risk of developing clinically significant symptoms are suitable for administration of the present EGFR antibodies. A clinician skilled in the art can readily determine, for example, by the use of clinical tests, physical examination and medical/family history, if an individual is a candidate for such treatment.

The present anti-EGFR antibodies can be administered for therapeutic treatments to a patient suffering from a tumor or angiogenesis associated pathologic condition in an amount sufficient to prevent, inhibit, or reduce the progression of the tumor or pathologic condition. Progression includes, e.g., the growth, invasiveness, metastases and/or recurrence of the tumor or pathologic condition. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. It should be noted, however, that the present invention is not limited to any particular dose.

A cocktail of EGFR antagonists, e.g., monoclonal antibodies, provides an especially efficient treatment for inhibiting the growth of tumor cells. The cocktail can include non-antibody EGFR antagonists and can have as few as 2, 3 or 4 receptor antagonists, and as many as 6, 8 or 10.

In an embodiment of the invention, anti-EGFR antibodies can be administered in combination with one or more anti-neoplastic agents. For examples of combination therapies, see, e.g., U.S. Pat. No. 6,217,866 (Schlessinger et al.) (Anti-EGFR antibodies in combination with a anti-neoplastic agents); WO 99/60023 (Waksal et al.) (Anti-EGFR antibodies in combination with radiation). Any suitable anti-neoplastic agent can be used, such as a chemotherapeutic agent, radiation or combinations thereof. The anti-neoplastic agent can be an alkylating agent or an anti-metabolite. Examples of alkylating agents include, but are not limited to, cisplatin, cyclophosphamide, melphalan, and dacarbazine. Examples of anti-metabolites include, but not limited to, doxorubicin, daunorubicin, paclitaxel, irinotecan (CPT-11), and topotecan. When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity tumor being treated and the route of administration of the agent. It should be emphasized, however, that the present invention is not limited to any particular dose.

For treatment of hyperproliferative disease, administration of the antibodies of the invention as described above can be combined with administration of any conventional treatment agent. For example, when the hyperproliferative disease is psoriasis, there are a variety of conventional systemic and topical agents available. Systemic agents for psoriasis include methotrexate, and oral retinoids, such as acitretin, etretinate, and isotretinoin. Other systemic treatments of psoriasis include hydroxyurea, NSAIDS, sulfasalazine, and 6-thioguanine. Antibiotics and antimicrobials can be used to treat or prevent infection that can cause psoriasis to flare and worsen. Topical agents for psoriasis include anthralin, calcipotriene, coal tar, corticosteroids, retinoids, keratolytics, and tazarotene. Topical steroids are one of the most common therapies prescribed for mild to moderate psoriasis. Topical steroids are applied to the surface of the skin, but some are injected into the psoriasis lesions.

Hyperproliferative disease treatments further include administration of anti-EGFR antibodies in combination with phototherapy. Phototherapy includes administration of any wavelength of light that reduces symptoms of the hyperproliferative disease, as well as photoactivation of a chemotherapeutic agent (photochemotherapy). For further discussion of treatment of hyperproliferative disorders, see WO 02/11677 (Teufel et al.) (Treatment of hyperproliferative diseases with epidermal growth factor receptor antagonists).

Anti-EGFR antibodies of the invention can be administered with EGFR antagonists, and/or antagonists of other RTKs such as antibodies that block RTK ligands or otherwise neutralize the RTKs. Ligands of EGFR include, for example, EGF, TGF-α amphiregulin, heparin-binding EGF (HB-EGF) and betacellulin. EGF and TGF-α are thought to be the main endogenous ligands that result in EGFR-mediated stimulation, although TGF-α has been shown to be more potent in promoting angiogenesis. Accordingly, EGFR antagonists include antibodies that bind to such ligands and thereby block binding to and activation of EGFR.

An example of another such RTK is VEGFR. In an embodiment of the present invention, an anti-EGFR antibody is used in combination with a VEGFR antagonist. In one embodiment of the invention, an anti-EGFR antibody is used in combination with a receptor antagonist that binds specifically to VEGFR-2/KDR receptor (PCT/US92/01300, filed Feb. 20, 1992; Termanet al., Oncogene 6: 1677-1683 (1991)). In another embodiment, an anti-EGFR antibody is used in combination with a receptor antagonist that binds specifically to VEGFR-1/Flt-1 receptor (Shibuya M. et al., Oncogene 5, 519-524 (1990)). Particularly preferred are antigen-binding proteins that bind to the extracellular domain of VEGFR-1 or VEGFR-2 and block binding by ligand (VEGF or P1GF), and/or neutralize VEGF-induced or P1GF-induced activation. For example, Mab IMC-1121 binds to soluble and cell surface-expressed KDR. Mab IMC-1121 comprises the $V_H$ and $V_L$ domains obtained from a human Fab phage display library. (See WO 03/075840) In another example, ScFv 6.12 binds to soluble and cell surface-expressed Flt-1. ScFv 6.12 comprises the $V_H$ and $V_L$ domains of mouse monoclonal antibody MAb 6.12. A hybridoma cell line producing MAb 6.12 has been deposited as ATCC number PTA-3344.

Another example of such an RTK is insulin-like growth factor receptor (IGFR). In certain tumor cells, inhibition of EGFR function can be compensated by upregulation of other growth factor receptor signaling pathways, and particularly by IGFR stimulation. Further, inhibition of IGFR signaling results in increased sensitivity of tumor cells to certain therapeutic agents. Stimulation of either EGFR or IGFR results in phosphorylation of common downstream signal transduction molecules, including Akt and p44/42, although to different extents. Accordingly, in an embodiment of the invention, an IGFR antagonist (e.g., an antibody that binds to IGF or IGFR and neutralizes the receptor) is coadministered with an antibody of the invention, thereby blocking a second input into the common downstream signaling pathway (e.g., inhibiting activation of Akt and/or p44/42). An example of a human antibody specific for IGFR is IMC-A12 (See WO 2005/016970).

Other examples of growth factor receptors involved in tumorigenesis are the receptors for platelet-derived growth factor PDGF), nerve growth factor (NGF), and fibroblast growth factor (FGF).

The anti-EGFR antibodies can also be administered with intracellular RTK antagonists that inhibit activity of RTKs or their associated downstream signaling elements that are involved in tumor growth or tumor-associated angiogenesis. The intracellular RTK antagonists are preferably small molecules. Some examples of small molecules include organic compounds, organometallic compounds, salts of organic compounds and organometallic compounds, and inorganic compounds. Atoms in a small molecule are linked together via covalent and ionic bonds; the former is typical for small organic compounds such as small molecule tyrosine kinase inhibitors and the latter is typical of small inorganic compounds. The arrangement of atoms in a small organic molecule may represent a chain, e.g. a carbon-carbon chain or carbon-heteroatom chain or may represent a ring containing carbon atoms, e.g. benzene or a policyclic system, or a combination of carbon and heteroatoms, i.e., heterocycles such as a pyrimidine or quinazoline. Although small molecules can have any moleculer weight they generally include molecules that would otherwise be considered biological molecules, except their molecular weight is not greater than 650 D. Small molecules include both compounds found in nature, such as hormones, neurotransmitters, nucleotides, amino acids, sugars, lipids, and their derivatives as well as compounds made synthetically, either by traditional organic synthesis, bio-mediated synthesis, or a combination thereof. See e.g. Ganesan, *Drug Doscov. Today* 7(1): 47-55 (January 2002); Lou, *Drug Discov. Today*, 6(2): 1288-1294 (December 2001).

More preferably, the small molecule to be used as an intracellular RTK antagonist according to the present invention is an intracellular EGFR antagonist that competes with ATP for binding to EGFR's intracellular binding region having a linase domain or to proteins involved in the signal transduction pathways of EGFR activation. Examples of such signal transduction pathways include the ras-mitogen activated protein kinase (MAPK) pathway, the phosphatidylinositol-3 kinase (PI3K)-Akt pathway, the stress-activated protein kinase (SAPK) pathway, and the signal transducers and activators of transcription (STAT) pathways. Non-limiting examples of proteins involved in such pathways (and to which a small molecule EGFR antagonist according to the present invention can bind) include GRB-2, SOS, Ras, Raf, MEK, MAPK, and matrix metalloproteinases (MMPs).

One example of a small molecule EGFR antagonist is IRESSA™ (ZD1939), which is a quinozaline derivative that functions as an ATP-mimetic to inhibit EGFR. See U.S. Pat. No. 5,616,582 (Zeneca Limited); WO 96/33980 (Zeneca Limited) at p. 4; see also, Rowinsky et al., Abstract 5 presented at the 37th Annual Meeting of ASCO, San Francisco, Calif. 12-15 May 2001; Anido et aL, Abstract 1712 presented at the 37th Annual Meeting of ASCO, San Francisco, Calif. 12-15 May 2001. Another examples of a small molecule EGFR antagonist is TARCEVA™ (OSI-774), which is a 4 -(substitutedphenylamino)quinozaline derivative [6,7-Bis (2-methoxy-ethoxy)-quinazolin-4-yl]-(3-ethynyl-phenyl) amine hydrochloride] EGFR inhibitor. See WO 96/30347 (Pfizer Inc.) at, for example, page 2, line 12 through page 4, line 34 and page 19, lines 14-17. See also Moyer et al., *Cancer Res.*, 57: 4838-48 (1997); Pollack et al., *J. Pharmacol.*, 291: 739-48 (1999). TARCEVA™ may function by inhibiting phosphorylation of EGFR and its downstream PI3/Akt and MAP (mitogen activated protein) kinase signal transduction pathways resulting in p27-mediated cell-cycle arrest. See Hidalgo et al., Abstract 281 presented at the 37th Annual Meeting of ASCO, San Francisco, Calif. 12-15 May 2001.

Other small molecules are also reported to inhibit EGFR, many of which are thought to being to the tyrosine kinase domain of an EGFR. Some examples of such small molecule EGFR antagonists are described in WO 91/116051, WO 96/30347, WO 96/33980, WO 97/27199(Zeneca Limited). WO 97/30034 (Zeneca Limited), WO 97/42187 (Zeneca Limited), WO 97/49688 (Pfizer Inc.), WO 98/33798 (Warner Lambert Company), WO 00/18761 (American Cyanamid Company), and WO 00/31048 (Warner Lambert Company). Examples of specific small molecule EGFR antagonists include C1-1033 (Pfizer), which is a quinozaline (N-[4-(3-chloro 4-fluoro-phenylamino)-7-(3-morpholin4-yl-propoxy)-quinazolin-6-yl]-acrylamide) inhibitor of tyrosine kinases, particularly EGFR and is described in WO 00/31048 at page 8, lines 22-6; PKI166 (Novartis), which is a pyrrolopyrimidine inhibitor of EGFR and is described in WO 97/27199 at pages 10-12; GW2016 (GlaxoSmithKline), which is an inhibitor of EGFR and HER2; EKB569 (Wyeth), which is reported to inhibit the growth of tumor cells that overexpress EGFR or HER2 in vitro and in vivo; AG-1478 (Tryphostin), which is a quinazoline small molecule that inhibits signaling from both EGFR and erbB-2; AG-1478 (Sugen), which is bisubstrate inhibitor that also inhibits protein kinase CK2; PD 153035 (Parke-Davis) which is reported to inhibit EGFR kinase activity and tumor growth, induce apoptosis in cells in culture, and enhance the cytotoxicity of cytotoxic chemotherapeutic agents; SPM-924 (Schwarz Pharma), which is a tyrosine kinase inhibitor targeted for treatment of prostrate cancer; CP-546,989 (OSI Pharmaceuticals), which is reportedly an inhibitor of angiogenesis for treatment of solid tumors; ADL-681, which is a EGFR kinase inhibitor targeted for treatment of cancer; PD 158780, which is a pyridopyrimidine that is reported to inhibit the tumor growth rate of A4431 xenografts in mice; CP-358,774, which is a quinzoline that is reported to inhibit autophosphorylation in HN5 xenografts in mice; ZD1839, which is a quinzoline that is reported to have antitumor activity in mouse xenograft models including vulvar, NSCLC, prostrate, ovarian, and colorectal cancers; CGP 59326A, which is a pyrrolopyrimidine that is reported to inhibit growth of EGFR-positive xenografts in mice; PD 165557 (Pfizer); CGP54211 and CGP53353 (Novartis), which are dianilnophthalimides. Naturally derived EGFR tyrosine kinase inhibitors include genistein, herbimycin A, quercetin, and erbstatin.

Further small molecules reported to inhibit EGFR and that are therefore within the scope of the present invention are tricyclic compounds such as the compounds described in U.S. Pat. No. 5,679,683; quinazoline derivatives such as the derivatives described in U.S. Pat. No. 5,616,582; and indole compounds such as the compounds described in U.S. Pat. No. 5,196,446.

In another embodiment, the EGFR antagonist can be administered in combination with one or more suitable adjuvants, such as, for example, cytokines (IL-10 and IL-13, for example) or other immune stimulators, such as, but not limited to, chemokine, tumor-associated antigens, and peptides. See, e.g., Larrivée et al., supra. It should be appreciated, however, that administration of only an anti-EGFR antibody is sufficient to prevent, inhibit, or reduce the progression of the tumor in a therapeutically effective manner.

In a combination therapy, the anti-EGFR antibody is administered before, during, or after commencing therapy with another agent, as well as any combination thereof, i.e., before and during, before and after, during and after, or before, during and after commencing the anti-neoplastic agent therapy. For example, the anti-EGFR antibody can be administered between 1 and 30 days, preferably 3 and 20 days, more preferably between 5 and 12 days before commencing radiation therapy. In a preferred embodiment of the invention, chemotherapy is administered concurrently with or, more preferably, subsequent to antibody therapy.

In the present invention, any suitable method or route can be used to administer anti-EGFR antibodies of the invention, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. The dose of antagonist administered depends on numerous factors, including, for example, the type of antagonists, the type and severity tumor being treated and the route of administration of the antagonists. It should be emphasized, however, that the present invention is not limited to any particular method or route of administration.

It is noted that an anti-EGFR antibody of the invention can be administered as a conjugate, which binds specifically to the receptor and delivers a toxic, lethal payload following ligand-toxin internalization. The antibody-drug/small molecule conjugate can be directly linked to each other or via a linker, peptide or non-peptide.

In another aspect of the invention, an anti-EGFR antibody of the invention can be chemically or biosynthetically linked to one or more anti-neoplastic or anti-angiogenic agents.

The invention further contemplates anti-EGFR antibodies to which target or reporter moieties are linked. Target moieties are first members of binding pairs. Anti-neoplastic agents, for example, are conjugated to second members of such pairs and are thereby directed to the site where the anti-EGFR antibody is bound. A common example of such a binding pair is avidin and biotin. In a preferred embodiment, biotin is conjugated to an anti-EGFR antibody, and thereby provides a target for an anti-neoplastic agent or other moiety, which is conjugated to avidin or streptavidin. Alternatively, biotin or another such moiety is linked to an anti-EGFR antibody of the invention and used as a reporter, for example in a diagnostic system where a detectable signal-producing agent is conjugated to avidin or streptavidin.

It is understood that the anti-EGFR antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The present invention also includes kits for inhibiting tumor growth and/or tumor-associated angiogenesis comprising a therapeutically effective amount of a human anti-EGFR antibody. The kits can further contain any suitable antagonist of, for example, another growth factor receptor involved in tumorigenesis or angiogenesis (e.g., VEGFR-1/Flt-1, VEGFR-2, PDGFR, IGFR,-NGFR, FGFR, etc, as described above). Alternatively, or in addition, the kits of the present invention can further comprise an anti-neoplastic agent. Examples of suitable anti-neoplastic agents in the context of the present invention have been described herein. The kits of the present invention can further comprise an adjuvant; examples have also been described above.

Moreover, included within the scope of the present invention is use of the present antibodies in vivo and in vitro for investigative or diagnostic methods, which are well known in the art. The diagnostic methods include kits, which contain antibodies of the present invention.

Accordingly, the present receptor antagonists thus can be used in vivo and in vitro for investigative, diagnostic, prophylactic, or treatment methods, which are well known in the art. Of course, it is to be understood and expected that variations in the principles of invention herein disclosed can be made by one skilled in the art and it is intended that such modifications are to be included within the scope of the present invention.

Increased EGFR activation is sometimes associated with the conditions that are treated according to the present invention. Higher levels of ligand, EGFR gene amplification, increased transcription of the receptor or mutations that cause unregulated receptor signaling can result in increased EGFR activation. Amplification of the gene encoding EGFR also results in an increased number of ligands binding to the EGFR, which can further stimulate cell proliferation. EGFR may be overexpressed in the absence of gene amplification, presumably through mutations that increase EGFR transcription, MRNA translation, or stability of the protein. EGFR mutants have been identified in gliomas, non-small-cell lung carcinomas, ovarian carcinomas and prostate carcinomas that have a constitutively active tyrosine kinase, suggesting a role for high-level EGFR activity rather than EGFR overexpression in these cancers. See, e.g., Pedersen et al., *Ann. Oncol.,* 12(6):745-60 (2001). (Type III EGFR mutation—variously named EGFRvIII, de2-7 EGFR or AEGFR—lacks a portion of the extracellular ligand binding domain encoded by exons 2-7.); see also Wikstrand et al., *Cancer Res.,* 55:3140-3148 (1995).

EXAMPLES

The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J. et al., Molecular Cloning: A Laboratory Manual, $2^{nd}$ ed., Cold Spring Harbor Laboratory Press (1989). All references mentioned herein are incorporated in their entirety.

Example 1

Isolation of Human Anti-EGFR Antibodies

Briefly, the human antibodies were isolated from a human naïve Fab bacteriophage library, obtained from Dyax, Cambridge, Mass. by biopanning against soluble human EGFR isolated from EGFR-positive tumors. The naïve Fab bacteriophage library containing the heavy and light chain variable regions of the antibody producing cells of human (peripheral B lymphocytes) was constructed from naïve uninimunized humans and tumor-free spleen cells from a patient with gastric carcinoma by amplifying in primary PCR reactions using V gene specific forward and backward primers and cloning these individual $V_H$ and $V_L$ genes into separate vectors (WO 00/70023).

The Fab library stock was grown to log phase, rescued with M13K07 helper phage and amplified overnight in 2YTAK medium (2YT containing 100 μg/ml of ampicillin and 50 μg/ml of kanamycin) at 30° C. The phage preparation was precipitated in 4% PEG/0.5M NaCl, resuspended in 3% fat-free milk/PBS to block nonspecific binding.

Approximately 1 $10^{12}$ pfu pre-blocked phage were incubated with $10^6$ EGFR-overexpressing A431 cells in 1 ml plain DMEM medium at 4° C. for 1 h, after which cells were washed 15 times with PBS. The bound phage were eluted by incubation at RT for 30 min with 1 ml PBS containing IMC- C225 at 0.5 mg/ml. The eluted phage were incubated with 10 ml of mid-log phase TG1 cells at 37° C. for 30 min stationary and 30 min shaking. The infected TG1 cells were pelleted and plated onto several large 2YTAG plates and incubated overnight at 30° C. All the colonies grown on the plates were scraped into 3 to 5 ml of 2YTA medium, mixed with glycerol (10% final concentration), aliquoted, and strored at −70° C. For the next round selection, 100 µl of the phage stock was added to 25 ml of 2YTAG medium and grown to mid-log phase. The culture was rescued with M13K07 helper phage, amplified, precipitated, and used for selection following the procedure described above.

Individual TG1 clones recovered after each round of selection were randomly picked and grown at 37° C. in 96-well plates and rescued with M13K07 helper phage as described above. The phage preparation was blocked with ⅙ volume of 18% milk/PBS at RT for 1 h and added to Maxi-sorp 96-well microtiter plates (Nunc) coated with recombinant EGFR (1 µg/ml×100 µl). After incubation at RT for 1 h, the plates were washed three times with PBST and incubated with a mouse anti-M13 phage-HRP conjugate (Amersham Pharmacia Biotech, Piscataway, N.J.). The plates were washed five times, TMB peroxidase substrate (KPL, Gaithersburg, Md.) added, and the absorbance at 450 nm read using a microplate reader (Molecular Devices, Sunnyvale, Calif.).

Identified clones were further tested for blocking of EGF binding. DNA fingerprinting of clones was used to differentiate unique clones. Representative clones of each digestion pattern were picked and subject to DNA sequencing.

Example 2

Expression and Purification of the Soluble Fab Fragments

Plasmids containing the genes encoding the 11F8 Fab were used to transform a nonsuppressor *E. coli* host HB2151. Expression of the Fab fragments in HB2151 was induced by culturing the cells in 2YTA medium containing 1 mM isopropyl-1-thio-β-D-galactopyranoside (IPTG, Sigma) at 30° C. A periplasmic extract pf the cells was prepared by resuspending the cell pellet in 25 mM Tris (pH 7.5) containing 20% (w/v). sucrose, 200 mM NaCl, 1 mM EDTA, and 1 mM PMSF, followed by incubation at 4° C. with gentle shaking for 1 h. After centrifugation, the soluble Fab protein was purified from the supernatant by affinity chromatography using a Protein G column, following the manufacturer's protocol (Amersham Pharmacia Biotech).

Example 3

Construction of Human Anti-EGFR IgG1 Antibodies

The human anti-EGFR Fab was engineered into a full human IgG1. A selected Fab candidate, C11F8, was identified from a human naïve Fab phage display library for high affinity binding to, and ligand blocking activity of human EFGR (ErbB). The DNA sequences encoding the variable regions of the 11F8 Fab light (SEQ ID NO:15) and heavy chain genes were obtained (SEQ ID NO:7) by PCR amplification and cloned into an expression vector containing the human IgG$_1$, constant domains using the glutamine synthase expression system from Lonza Biologics, Inc.

PCR amplification was performed in two steps utilizing the Expand PCR kit (Boe lringer Mannheim, Inc.) according to the manufacturer's specifications and the primers listed in Table 3.

TABLE 3

PCR Amplification Primers

| Primer | Nucleotide Sequence | SEQ ID NO: |
|---|---|---|
| C11F8HF | 5' TCCTTTTTCTAGTAGCAACTGCAACTGGAGTACATT CACAGGTGCAGCTGCAGAA-3' | 20 |
| C11F8HR | 5'-CGAGCTAGCGCTTGAGACGGTGACCAGGGTG-3' | 21 |
| C11F8LF | 5'-TCCTTTTTCTAGTAGCAACTGCAACTGGAGTACATT CAGAAATTGTGATGACACA-3' | 22 |
| C11F8LR | 5'-CGATCTAGAACTCACGTTTGATCTCCGCCTTGGTC-3' | 23 |
| OSIF | 5'-GAGAAGCTTGCCGCCACCATGGGATGGCATGTATCA TCCTTTTTCTAGTAGC-3' | 24 |

Briefly, the PCR products of heavy and light chains were amplified utilizing 25 ng C11F8 Fab plasmid DNA as template and the pair of forward and reverse primers for the heavy (C11F8HF and C11F8HR) and light chains (C11F8LF and C11F8LR) in 50 µL Expand Buffer System #3 reactions under the following cycling conditions in Table 4:

TABLE 4

| 1 cycle | 94° C. | 2 minutes |
|---|---|---|
| 5 cycles | 94° C. | 20 seconds |
|  | 48° C. | 2 minutes |
|  | 68° C. | 20 seconds |
| 20 cycles | 94° C. | 20 seconds |
|  | 65° C. | 60 seconds |
|  | 68° C. | 2 minutes |
| 1 cycle | 65° C. | 5 minutes |

The resulting PCR products add a 57-base pair sequence to the 5' end of the immunoglobulin genes encoding a 19-amino acid mouse heavy chain gene signal sequence (MGWSCIIL-FLVATATGVHS, SEQ ID NO:25), which enables efficient immunoglobulin processing and secretion. For efficient initiation of translation of genes in mammalian cells, a consensus "Kozak" sequence (*J. MoL Biol.* 196:947) was added by amplifying the heavy and light chain in a secondary PCR reaction using the forward primer, OSIF in combination with CH11F8HR or C11F8LR respectively. This PCR product also provides a 5' Hind III restriction endonuclease site for cloning of the amplified product into suitable expression vector, Agarose gel-purified Hind III-Nhe I heavy chain fragment was cloned into a CMV promoter-driven vector, pDFc (FIG. 1A) to generate a contiguous cDNA coding region of variable and constant region DNA sequence. A Hind III-Xba I light chain fragment was cloned into a second CMV promoter-driver vector, p12.1L (FIG. 1B). The resulting construct contains a single intron separating the variable light and kappa constant regions, which is efficiently spliced from nascent RNA transcript. The recombinant plasmids were transformed into competent *E. coli* and selected plasmid isolates were screened for transient co-expression of the heavy and light chains in COS cells.

Example 4

Expression of Human Anti-EGFR IgG1 Antibodies

For stable transfection, a single plasmid vector was generated by cloning the Not I-Sal I fragment of the CMV promoter-containing heavy chain expression cassette into the light chain-containing p12.1L vector. The resulting plasmid vector, pGS-11F8 was restriction mapped (see, FIG. 1C). The restriction digest analysis was shown in FIG. 2.

The recombinant cell line used for the production of 11F8 monoclonal antibody is derived from the non-secreting murine myeloma cell line, NS0 (refered to in Barnes et al., Cytotechnology 32:109 (2000)). The NS0 cell line was obtained from Lonza Biologics, Inc. (Slough, Berkshire, UK).

The myeloma cell line, NS0 was transfected with plasmid, pGS-11F8 via electroporation using the BioRad Gene Pulser II, set at a voltage of 250V with a capacitance of 400 μFd and an observed time constant of 9.0 msec. The electroporated cells were resuspended in DMEM (JRH Biosciences, Inc., Lenexa, Kans.) containing 10% dialyzed fetal calf serum, dFCS (HyClone, Logan, Utah) and 2 mM glutamine (InVitrogen/Life Technologies, Paisley, Pa.). 50 μl of the resuspended cells were seeded into 96-well plates at a density of 5,000-10,000 cells per well. Glutamine synthetase (GS)-positive transfectants were selected by addition of glutamine-free DMEM medium containing 10% DFCS, supplemented with 1×GS (JRH Biosciences, Inc.) 24-h post-transfection. Cells were cultured for 2-4 weeks at 37° C., 5% $CO_2$ to enable growth and expansion of colonies prior to screening for antibody-expressing clones.

Clones expressing anti-EGFR antibody were screened using a horseradish peroxidase anti-human Fc (gamma)-based ELISA and detection was carried out at $A_{450nm}$. Positive clones were expanded and retested over 3-5 days cultivation period. Strong positives (antibody production of 25 μL/mg or more) were expanded for further analysis. Based on antibody batch production results of 249 μg/mL, Clone #34 was selected for limiting dilution sub cloning and reassessed. Clone 34-5 was selected based on consistent production levels, comparable to or better than the parent cell line (batch production =310 μg/mL, fed-batch=0.75-0.8 g/L). Clone #34-5-3 was isolated after a second round of subcloning and analysis showed that Clone #34-5-3 produces a high level of antibody (batch production=324 μg/mL, fed-batch=1.0-1.2 g/L). Further characterization of this clone was carried out in the following examples.

Example 5

In Vitro Binding of Antibodies to EGFR

Antibodies were screened in a solid state ELISA comparing the binding characteristics of IMC-11F8 and IMC-C225. Ninety six-well microtiter plate was coated overnight with 1 μg/mL in carbonate buffer at 4° C. Plates were blocked with phosphate buffered saline (PBS) supplemented with 10% new born calf serum for one hour at 37° C. Various amounts of IMC-11F8 or IMC-C225 were added to the plates and incubated at room temperature for a further 60 minutes, followed by washing with PBS. Mouse anti-human Fc antibody-horse radish peroxidase (HRP) conjugate were added and incubated for an additional 60 minutes at room temperature, followed by extensive washing with PBS. The plate was then incubated with HRP substrate for 30 sec.-2 min. and the reaction stopped with 0.1 M $H_2SO_4$. The plates were read using an ELISA reader at $OD_{450nm}$.

Figure 3:
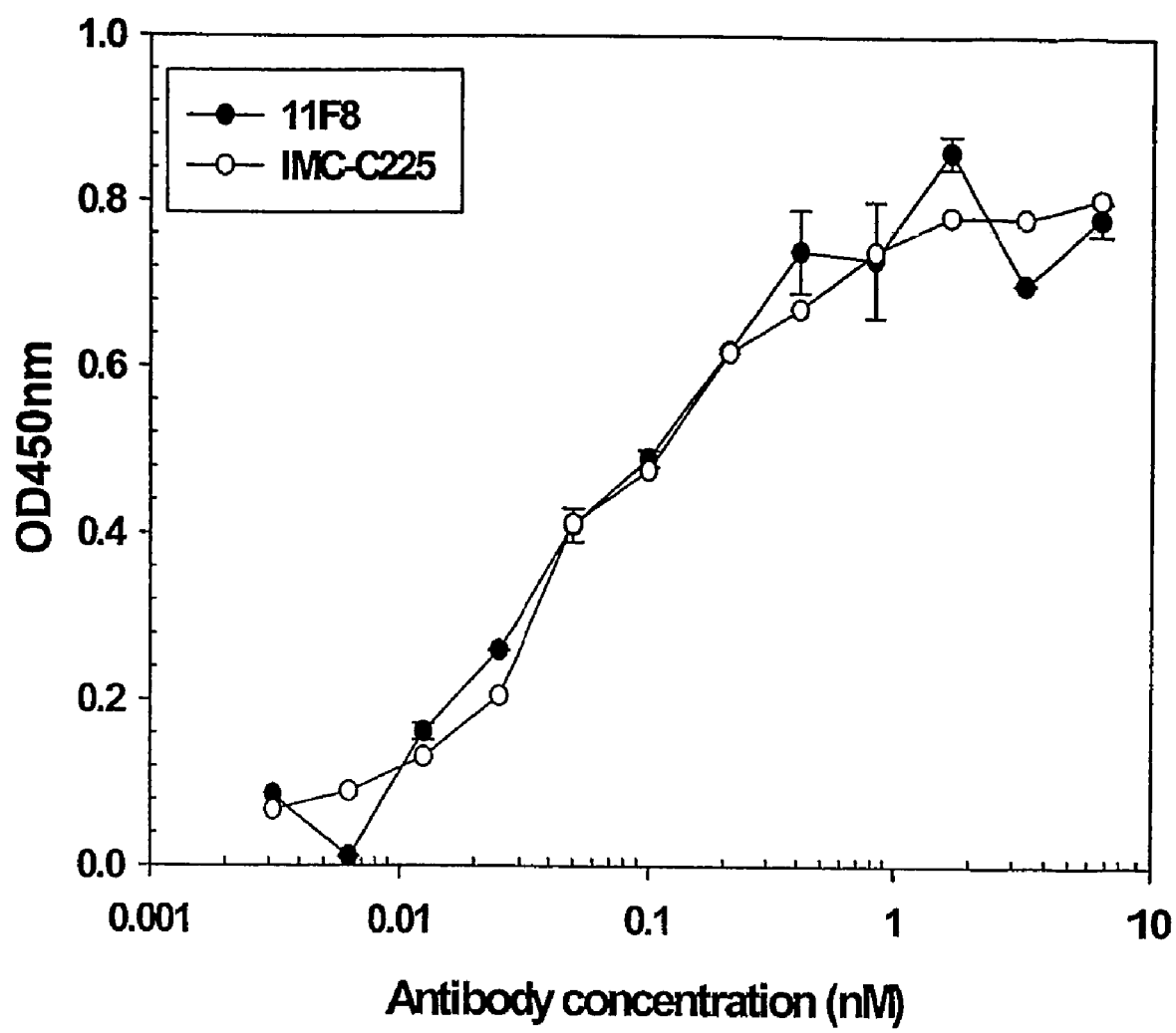
FIG. 3 shows in-vitro binding of IMC-C11F8 and IMC-C225 to EGFR as measured by ELISA.

FIG. 3 shows the binding of IMC-11F8 and IMC-C225 antibodies to EGFR. Both IMC-11 F8 and IMC-C225 exhibit comparable binding to EGFR.

Example 6

Binding Kinetics of Anti-EGFR Antibodies

The binding kinetics of IMC-11F8 and IMC-C225 IgG antibodies and their respective Fab fragments were measured using a BIAcore sensor (Pharmacia Biosensor,) EGFR-AP fusion protein was immobilized onto a sensor chip and soluble IMC-11F8 and IMC-C225 antibodies were injected at concentrations ranging from 1.5 nM to 100 nM. Sensorgrams were obtained at each concentration and were analyzed with BIA Evaluation 2.0, a program to determine the rate constants, $k_{on}$ and $k_{off}$. The affinity constant, Kd, was calculated from the ratio of rate constants, $k_{off}/k_{on}$.

The binding kinetics of the anti-EGFR antibodies of the present invention are illustrated in Table 5. These show that both IgG antibodies have comparable binding kinetics to EGFR.

TABLE 5

| Antibody | Format | $k_{on}$ ($10^5 M^{-1}s^{-1}$) | $k_{off}$ ($10^{-4} s^{-1}$) | $K_d$ (nM) |
| --- | --- | --- | --- | --- |
| IMC-11F8 | Fab | 22.9 ± 9.9 | 36.7 ± 8.5 | 1.78 ± 0.5 |
| IMC-11F8 | IgG | 18.6 ± 7.7 | 5.8 ± 2.2 | 0.32 ± 0.06 |
| IMC-C225 | Fab | 23.1 ± 4.8 | 11.7 ± 3.4 | 0.53 ± 0.17 |
| IMC-C225 | IgG | 21.3 ± 7.3 | 5.4 ± 1.0 | 0.3 ± 0.2 |

The results represent the mean ± SE from at least three separate determinations.

Example 7

Specificity of the Antibodies for EGFR

Antibody binding to EGFR was evaluated by a $^{125}$I-EGF competition assay. HT29 cells were seeded at $2 \times 10^4$ cells per well in 24-well COSTAR™ plates (Fisher Scientific, U.S.A.) in McCoy's 5a medium supplemented with 1.5 mM L-glutamine, 10% CS and antibiotics at 37° C. The cell monolayer was then incubated at room temperature for 1 hour with various concentrations of unlabeled EGF, 11F8 or IMC-C225 that were mixed with various amounts of $^{125}$I-labeled EGF. Cells were washed with cold PBS and cell-associated radio-activity was measured in a gamma counter.

Figure 4:
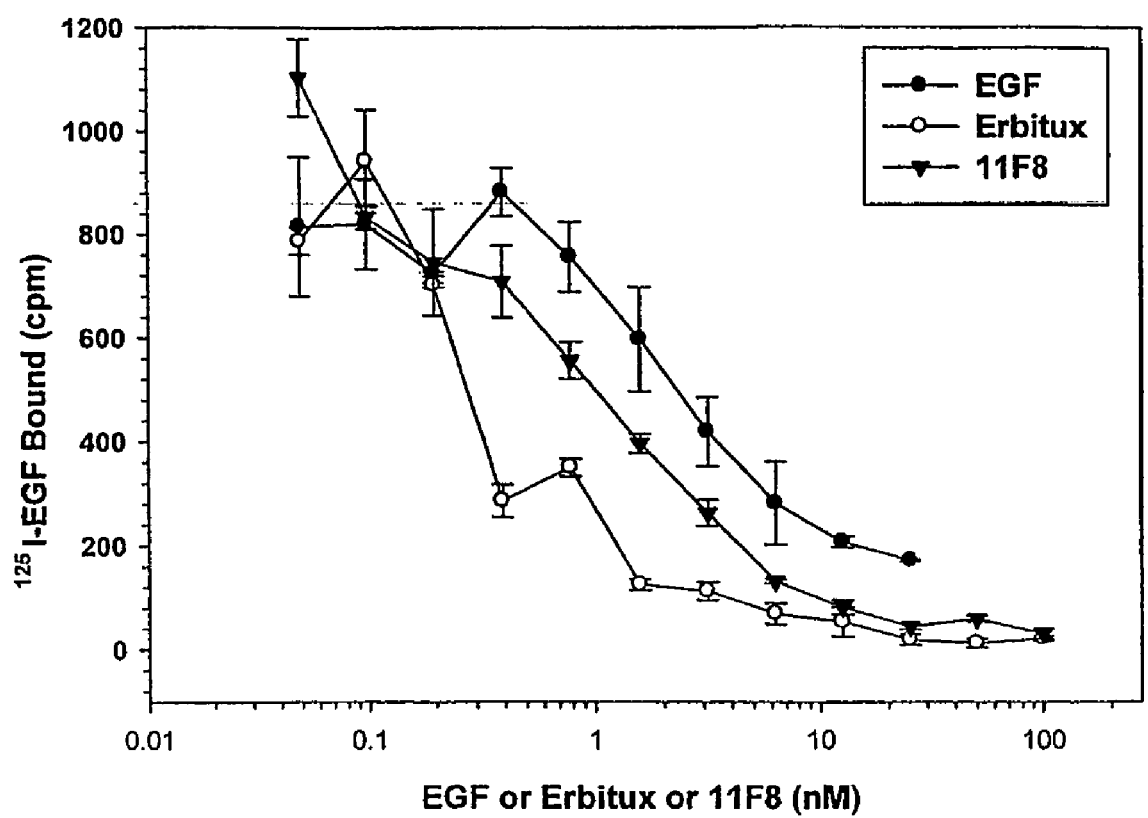
FIG. 4 shows in vitro competition results of IMC-11F8 and IMC-C225 with $^{125}$I-labeled EGF for EGFR binding.

FIG. 4 shows the inhibition of $^{125}$I-EGF binding to EGFR on HT29 cells. At concentrations of between 10 to 100nM, IMC-11F8 is as efficient as IMC-C225 in inhibiting $^{125}$I-EGF binding to EGFR on HT29 cells. Both antibodies are better at competing for binding than EGF, the natural ligand of EGFR. Similar results were observed for inhibition of $^{125}$I-EGF binding to EGFR on A431 cells.

Example 8

EGFR Activation

Briefly, a kinase receptor activation assay (KIRA assay), or phosphorylation assay, was carried out using BxPC3 or A431 cells. Cells were first grown to 90% confluency in DME supplemented with 4 mM L-glutamine adjusted to contain 1.5 g/L sodium bicarbonate and 4.5 g/L glucose, 10% CS, at 37° C. Prior to experimentation, the cells were starved for 24 h in DME supplemented with 0.5% CS. To evaluate the effects of antibodies, IMC-11F8, IMC-C225 and IMC-1C11 on EGF-induced activation of EGFR, various concentrations of antibodies were prebound at room temperature for 30 minutes, followed by stimulation with EGF at 8 ng/mL for another 15 minutes. Following stimulation, cell monolayers were washed with ice cold PBS containing 1 mM sodium orthovanadate. Cells were lysed in lysis buffer [20 mM Tric-HCl, pH. 7.4, 1% Triton X-100, 137 mM NaCl, 10% glycerol, 10 mM EDTA, 2 mM sodium orthovanadate, 100 mM NaF, 100 mM sodium pyrophosphate, 5 mM PEFABLOC® SC (Boehringer Mannheim Biochemicals, Indianapolis, Ind.), 100 μg aprotinin and 100 μg/mL leupeptin] and centrifuged at 14,000×g for 10 minutes. Cleared cell lysates were added to wells of 96-well plates coated with polyclonal anti-EGFR antibody. The plates were washed to remove non-specifically bound proteins and the level of EGFR phosphorylation was assessed by the addition of anti-phosphotyrosine antibody. Upon extensive washing, the amount of bound anti-phoshotyrosine antibody was measure using an ELISA reader at $OD_{450nm}$.

Figure 5:
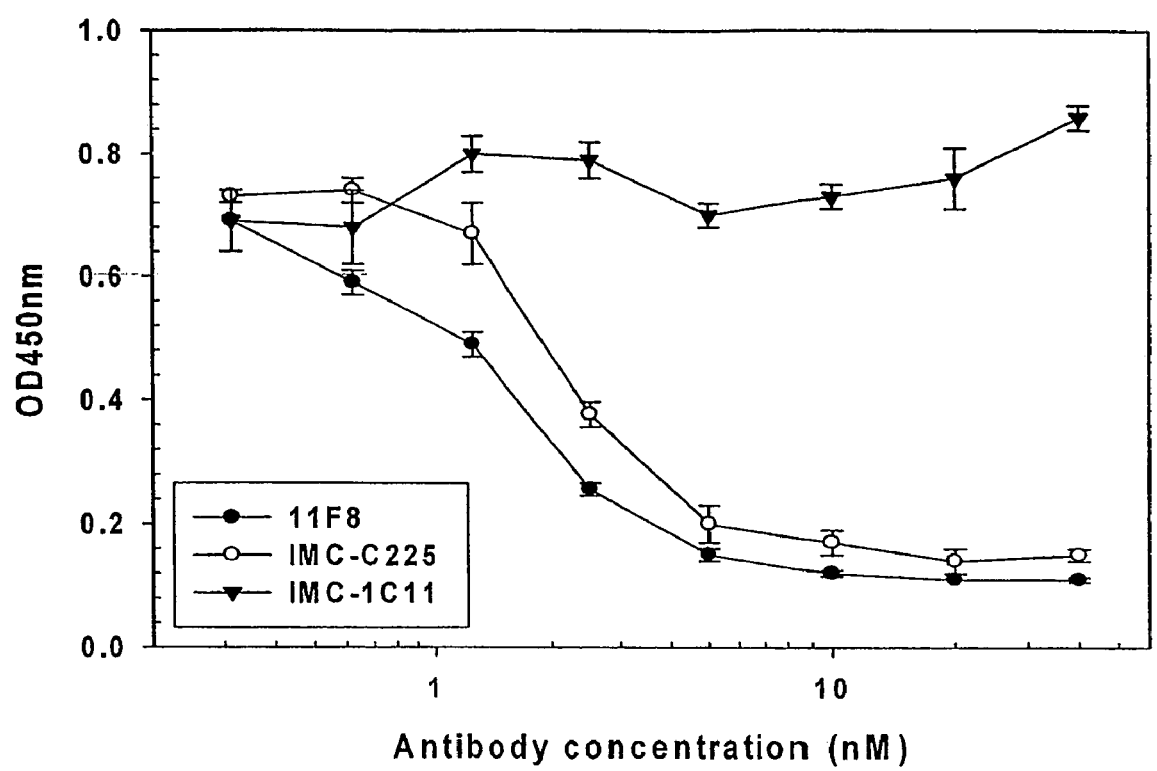
FIG. 5 shows effects of IMC-11F8 and IMC225 on the phosphorylation of EGFR in BxPC3 cells. Control antibody used is IMC-1C11.
Figure 6:
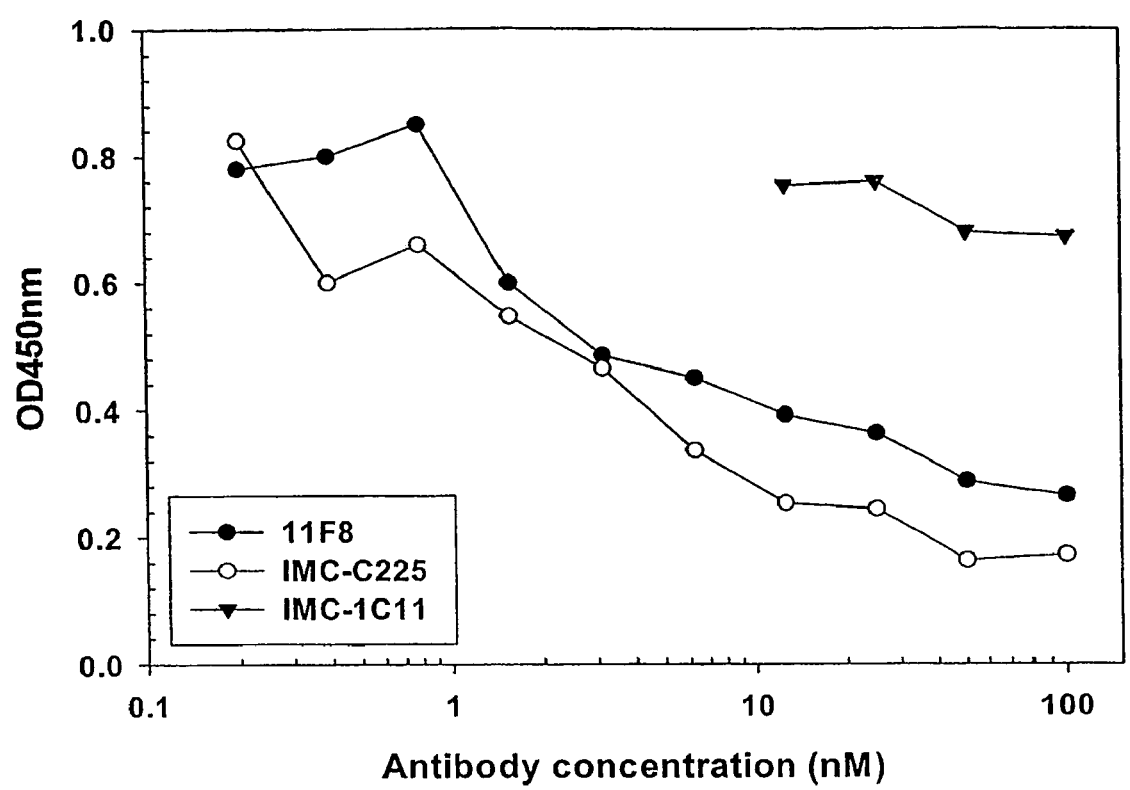
FIG. 6 shows inhibition of EGFR phosphorylation by IMC-11F8 and IMC-C225 in A431 cells.

The results show a marked decrease in phosphorylation of EGFR by IMC-11F8 antibody in both BxPC3 (FIG. 5) and A431 (FIG. 6) cells tested as compared to control antibody, IMC-1C1.

Inhibition of EGF-stimulated EGFR phosphorylation was further evaluated by Western blot analysis of the immunoprecipitated EGFR. A431 cells were prebound with antibodies followed by stimulation with EGF as described above. A control antibody that binds to EGFR but does not inhibit EGFR phosphorylation was used. Protein (EGFR) was immunoprecipitated from the cleared lysates using polyclonal anti-EGFR antibody followed by Protein A Sepharose beads. The bound-beads were then washed once with 0.2% Triton X-100, 10 mM Tris-HCl, pH 8.0, 150 mM NaCl, 2 mnM EDTA (Buffer A), twice with Buffer A containing 500 mM NaCl and twice with Tris-HCl, pH 8.0. Drained beads were mixed with 30 μL 2×SDS loading buffer, boiled and the supernatant was subjected to SDS-PAGE. After separation of proteins by electrophoresis, the protein bands were transferred onto nitrocellulose filters for Western Blot analysis. Filters were blocked overnight in blocking buffer, 50 mM Tris-HCl, pH7.4, 150 mM NaCl (TBS) containing 5% bovine serum albumin and 10% nonfat dried milk. To detect phosphorylated receptor, blots were probed with an anti-phosphotyrosine antibody in blocking buffer for 1 hour at room temperature. Blots were then washed extensively with 0.5×TBS containing 0.1% Tween-20 (TBS-T) and incubated with goat anti-mouse Ig conjugated to HRP (Ainersham, Little Chalfont, U.K.). Blots were washed with TBS and incubated for 1 minute with a chemiluminescence reagent (ECL, Amersham, Little Chalfont, U.K.). Anti-phosphotyrosine reacting with phosphorylated proteins was detected by exposure to a high performance luminescence detection film (Hyperfilm-ECL, Arnersham, Little Chalfont, U.K.) for 0.5 to 10 minutes.

Figure 8:
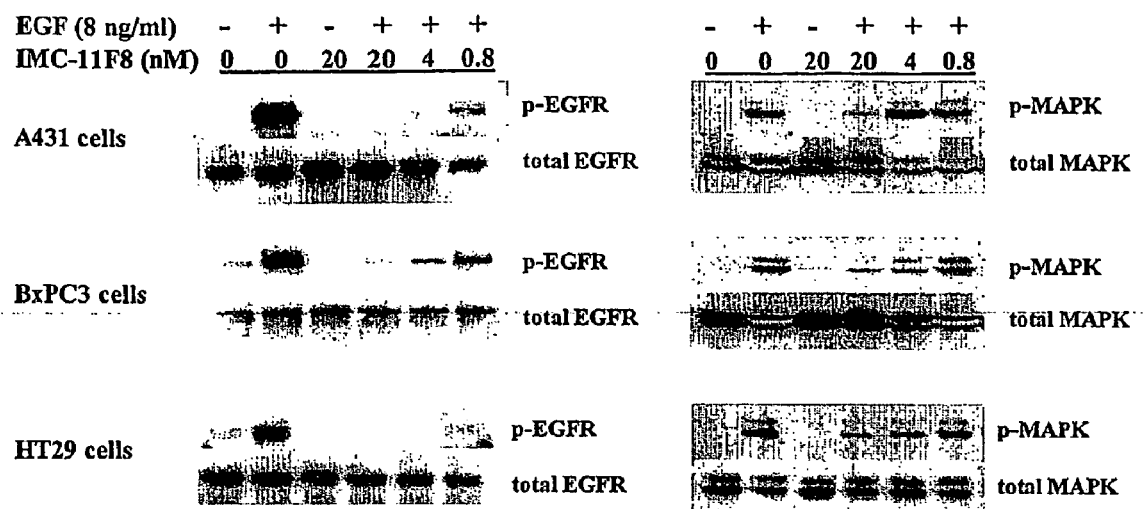
FIG. 8 shows inhibition of EGF-stimulated EGFR phosphorylation by various concentrations of IMC-11F8.

Western blot analysis in FIG. 7A shows that IMC-11F8, like IMC-C225, inhibits EGFR phosphorylation. Neither EGF-antibody nor the control antibody-treated cells completely inhibits EGFR phosphorylation. FIG. 7B shows that synthesis of EGFR is not inhibited with the addition of antibodies to the cells. FIG. 8 shows that phosphorylation of EGFR is inhibited by IMC-11F8. Greater than 70% inhibition was observed for three tumor cell lines of different origin (A431, BxPC3, HT-29) at the lowest antibody concentration tested (0.8 mM).

The effect of IMC-11F8 on one of the major downstream signaling molecules of EGFR, MAP kinases p44/p42, was also examined. IMC-11F8 blocked p44/42 MAP kinases phosphorylation following EGF stimulation in A431, BxPC3 and HT-29 cells in a dose-dependent manner (FIG. 4).

Example 9

Inhibition of Cell Proliferation

The MTT Cell Proliferation Assay is measured color-metrically as a result of reduction of the yellow tetrazolium, MTT (3-(4,5-dimethylthiazolyl-2)-2,5-phenyltetrazolium bromide) by metabolically active cell to an intracellular purple formazan product, which can be solubilized and quantified by spectrophotometric means. Briefly, DiFi cells were cultured overnight in DMEM-10% CS. Antibodies, IMC-11F8, IMC-C225 or IMC-1C11 were added to triplicate wells and incubated for an additional 72 hours at 37° C., 5% $CO_2$. To measure cell growth, a 20 μL aliquot of tetrazolium dye was added to each well and the cells were incubated for 3 hours at 37° C. When the purple precipitate was clearly visible under a microscope, the cells were lysed by addition of 100 μl detergent reagent. Absorbance of the formazan product was measured at $OD_{570nm}$ as a quantitation of proliferation.

Figure 9:
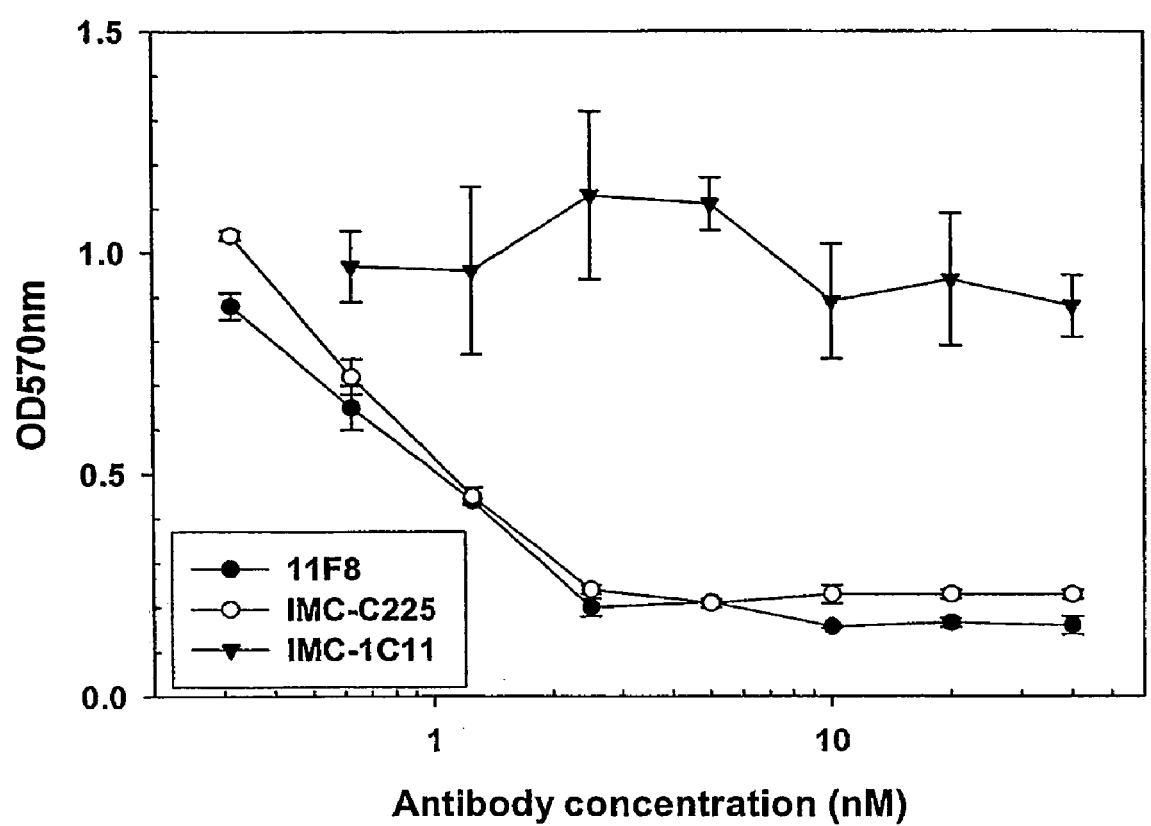
FIG. 9 shows inhibition of DiFi cell proliferation by IMC-11F8, IMC-C225 and control antibody, IMC-1C11 as assessed by an MTT assay.

As shown in FIG. 9, unlike control antibody IMC-1C11, IMC-11F8 is as potent an inhibitor of cell proliferation as IMC-C225.

Example 10

Antibody-Dependent Cellular Cytotoxicity (ADCC) Activity

One method of assessing cell death is via an antibody dependent cell-mediated cytotoxicity assay or ADCC, which generally use the radioisotope $^{51}Cr$. Target cells labeled with $^{51}Cr$ were mixed with antibody and the degree of killing was assessed by release of $^{51}Cr$. Briefly, approximately $3 \times 10^6$ DiFi cells were suspended in 0.5 μl culture medium and 0.5 mCi of $Na^{51}CrO_4$ was added. The mixture was incubated for 1 h at 37° C. with occasional shaking. The cells were then washed three times with cold culture medium. The labeled cells were then suspended in 100 μl culture medium containing varying concentrations of anti-EGFR antibodies (IMC-11F8 or IMC-C225) and incubated for 30 minutes at 4° C. The cells were then washed three times with culture medium by centrifugation. Rabbit complement was added and the treated cells were further incubated at 37° C. for 1 h. 50 μl of cold medium were then added and centrifuged. The supernatants were then removed and the radioactivity released by the cells into the supernatant was measured in a gamma counter. The maximum release of the radioactivity was obtained by adding 1% Triton X to the target cells. The percent cytotoxicity was calculated as cpm experimental release minus cpm background times 100%, which is then divided by the cpm maximum release minus cpm background.

Figure 10:
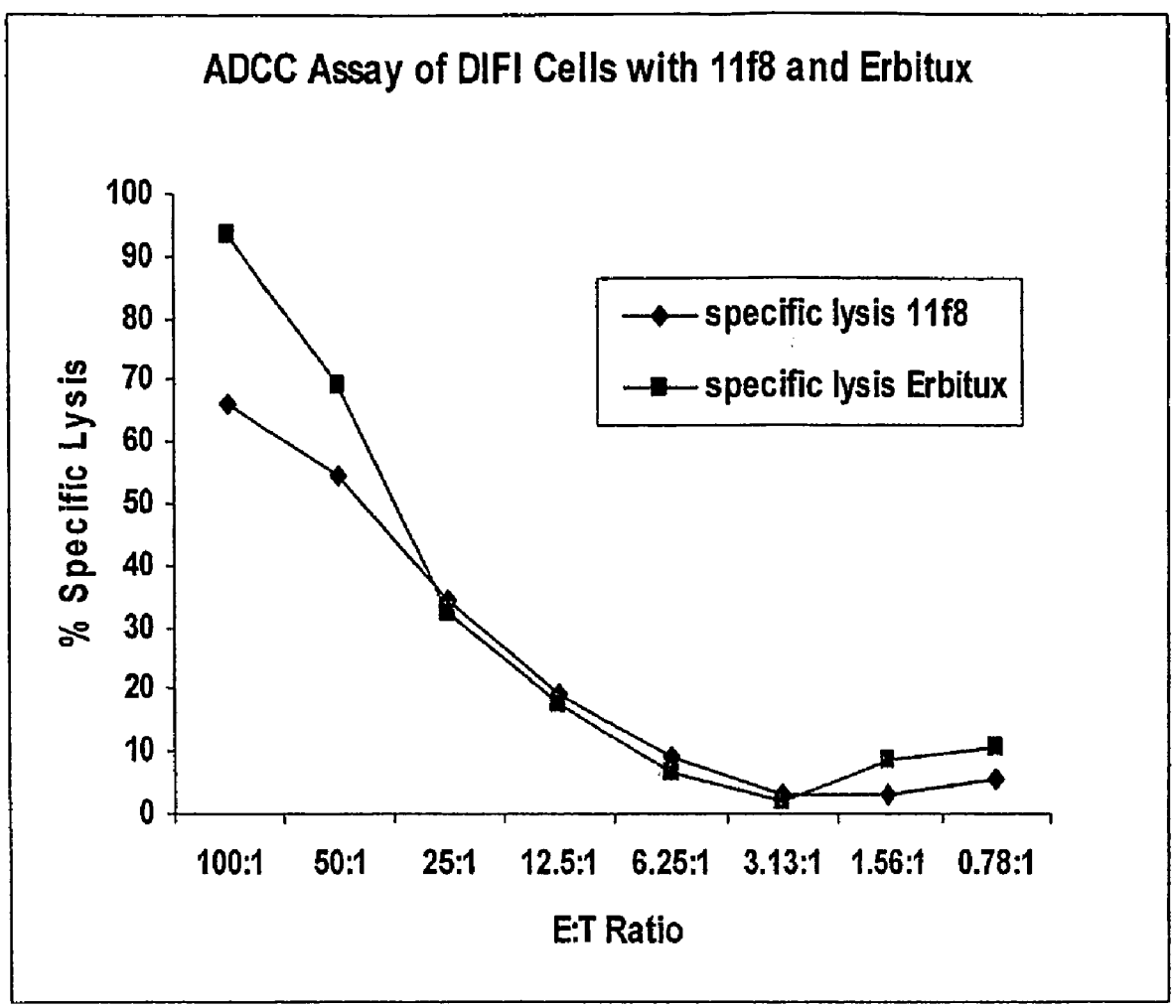
FIG. 10 shows the specific lysis of $^{51}$Cr-labeled DiFi cells treated with IMC-11F8 or IMC-C225 (ERBITUX™).

FIG. 10 shows IMC-11F8 and WC-C225 (or ERBITUX™) mediate cell death via activation of the Antibody Dependent Cellular Cytotoxicity or ADCC activity).

Example 11

In Vivo Inhibition of Tumor Cell Growth in Mice

In vivo anti-tumor studies were designed to determine if IMC-11F8 would block the growth of tumor cells in a xenograft model. Athymic mice (nu/nu; Charles River Lab, Wilmington, Mass.) were injected subcutaneously with 1-2 million A431 or BxPC-3 cells in the flank. Anti-EGFR antibodies (IMC-11F8 and IMC-C225) or control antibody was administered intraperitoneally at either 1 mg/dose or 0.3 mg/dose, three times per week. Tumor size was measured at least three times per week with a caliper and tumor volume calculated (See, e.g. Baselga et al., J Natl. Cancer Inst. (1993) 85:1327-1333)

Figure 11:
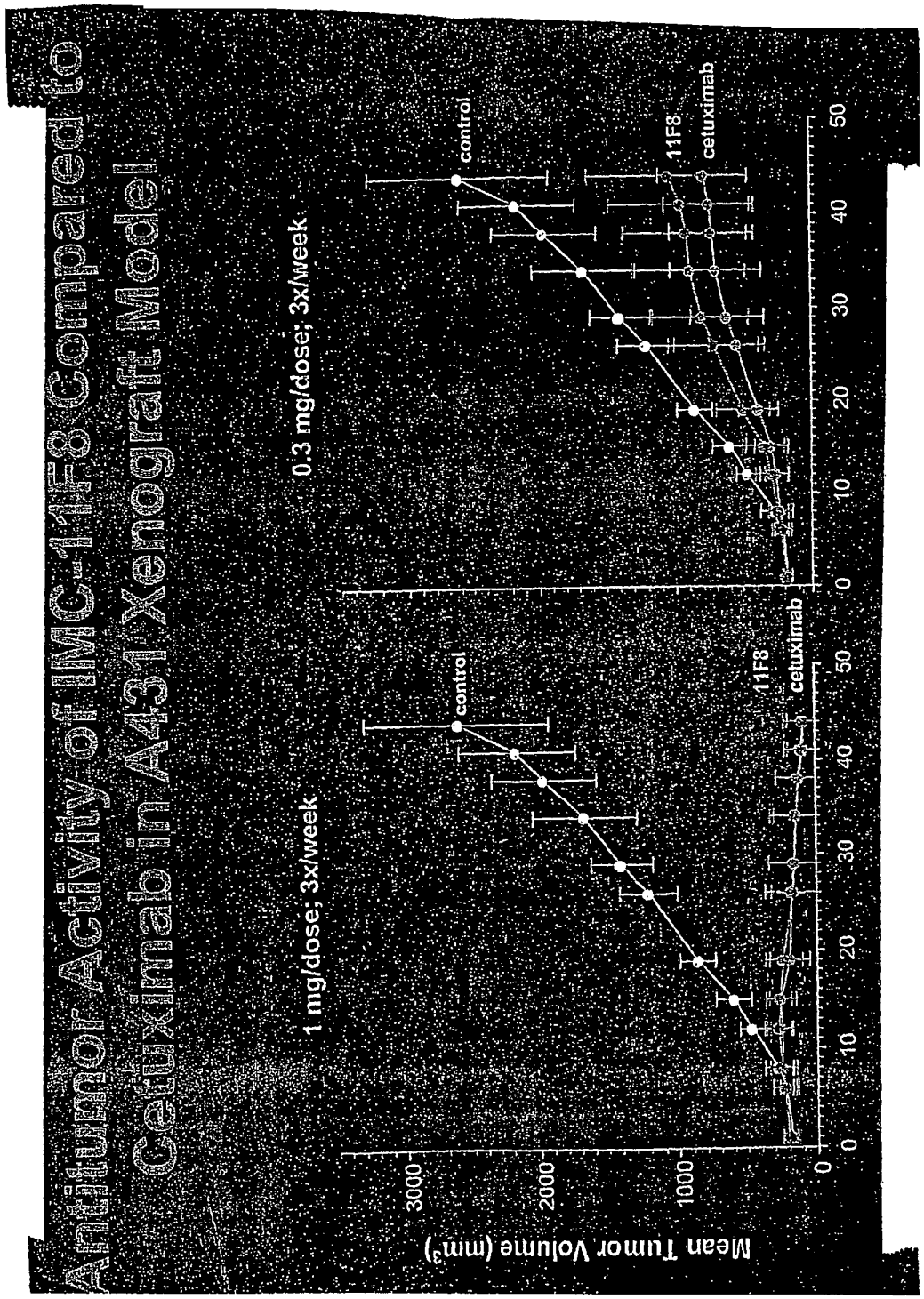
FIG. 11 shows the growth of A431 tumor cells in mice treated with either IMC-11F8 or IMC-C225 (Cetuximab). Untreated animals served as controls for tumor growth.
Figure 12:
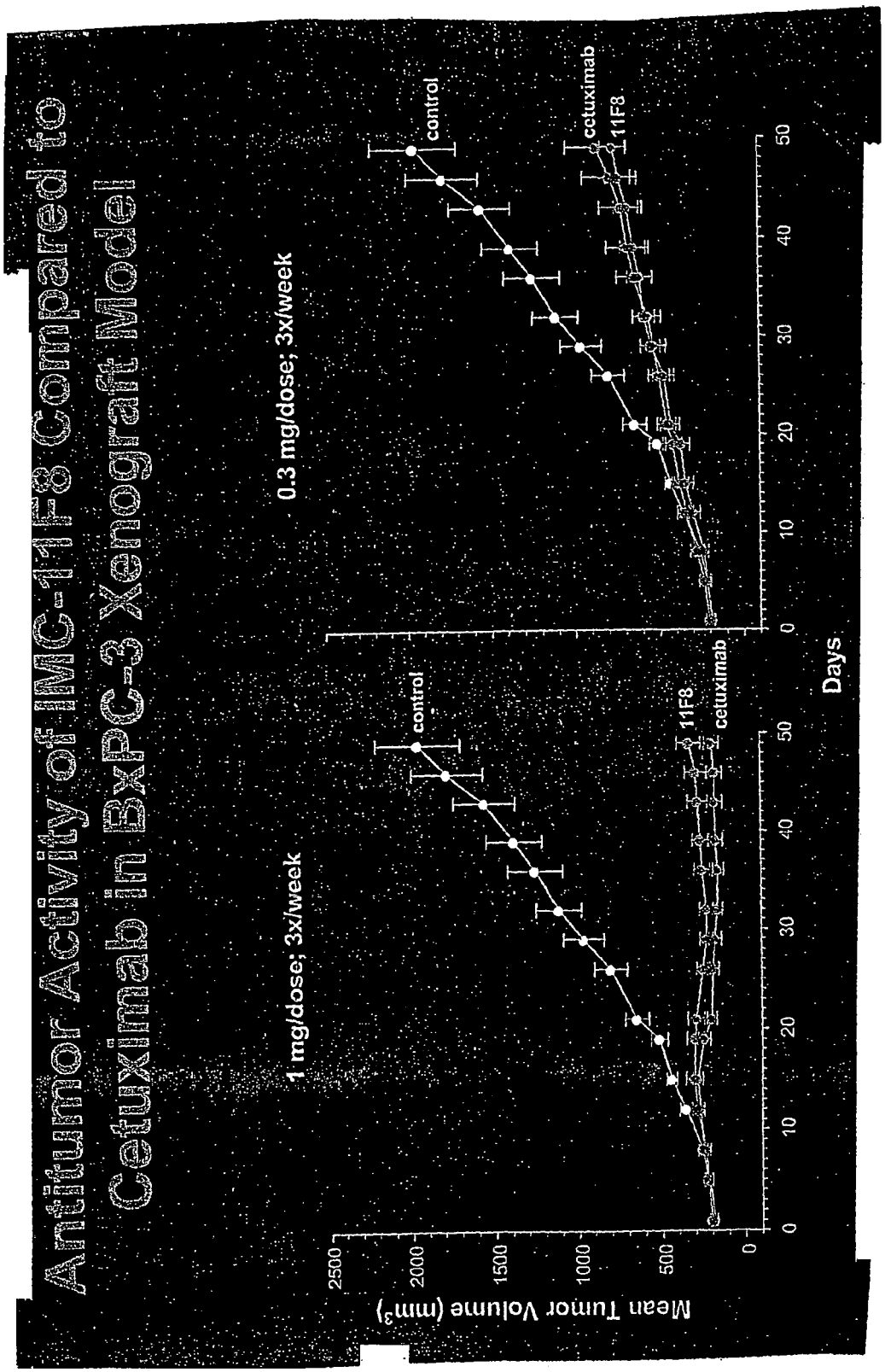
FIG. 12 shows the growth of BxPC3 tumor cells in mice treated with either IMC-11F8 or IMC-C225 (Cetuximab). Untreated animals served as controls for tumor growth.

FIG. 11 shows the anti-tumor activity of IMC-11F8 in A431 xenograft model. At 1 mg dose (FIG. 11, right panel, IMC-11F8 is as effective as IMC-C225 (CETUXIMAB) in suppressing or inhibiting tumor growth as compared to control animals. At a lower dose of 0.3 mg, progression of tumor growth is retarded. Similarly, FIG. 12 shows the effect of IMC-11F8 and IMC-C225 in a second tumor model (BxPC-3 xenograft). The kinetics of BxPC3 tumor growth is similar to that observed in the A431 tumor model. At the 1.0 mg/mouse/injection dose level IMC-11F8 led to 6 tumor regressions out of 8 A413-bearing animals, and 5 tumor regression out of 8 BxPC3-bearing mice.

Figure 13:
FIG. 13 shows immunohistochemical staining of xenografted human tumors from nude mice treated with saline or IMC-11F8. Panel A and B, A431 xenografts from nude mice treated with saline (A) or IMC-11F8 (B). Panel C and D, BxPC3 xenografts from nude mice treated with saline (C) or IMC-11F8 (D). Panel E and F, Ki-67 staining of A413 xenografts from nude mice treated with saline (E) or IMC-11F8 (F).
Figure 13:
Figure 13:
Figure 13:
Figure 13:
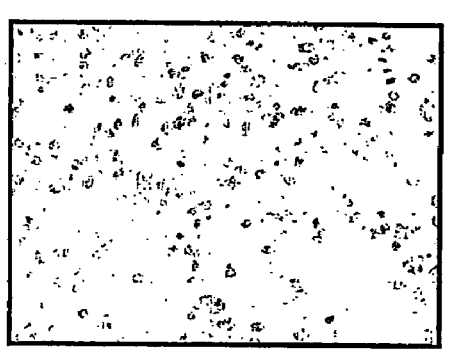
Figure 13:
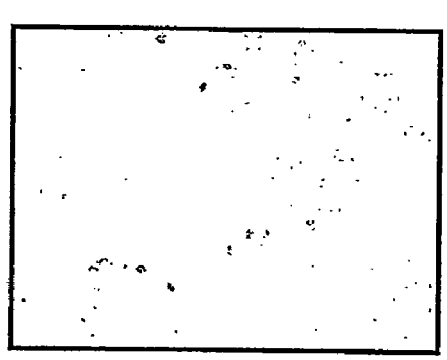

Immunohistochemistry staining of both A431 and BxPC3 xenograft sections revealed that IMC-11F8 treatment markedly reduced the tumor cell density and increased the area of necrotic acellular debris within the tumors (FIG. 13). Further, IMC-11F8 reduced the percentage of Ki-67 positive cells across the entire tumor section, indicating a reduction in cell proliferation within the tumors (FIG. 13).

Example 12

IMC-11F8 Combination Therapy

Nude mice bearing human colorectal tumor xenografts, GEO, DLD-1, or HT-29, of approximately 200-300 mm³ were treated by interperitoneal injection of IMC-11F8 twice a week at 0.3 mg or 1.0 mg/injection, alone or in combination with irinotecan (CPT-11) at a dose of 100 mg/kg once a week. Tumor sizes were measured twice a week.

Figure 14:
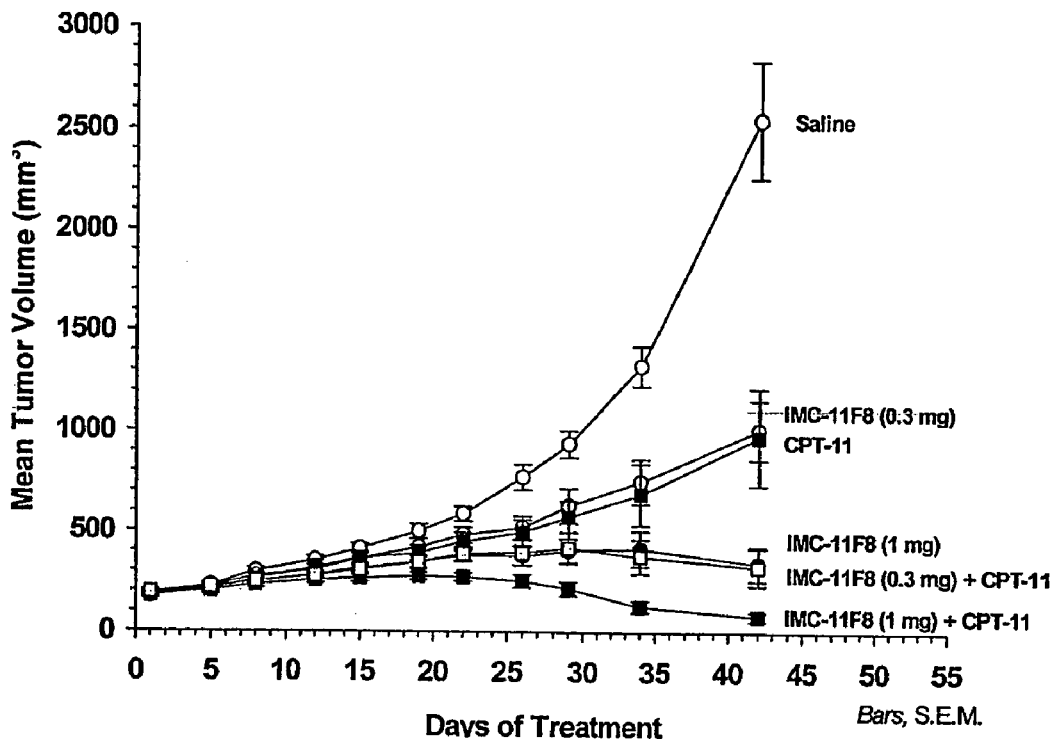
FIG. 14 shows inhibition of xenografted human colorectal carcinomas in nude mice by IMC-11F8 in combination with CPT-11. Nude mice bearing human colorectal tumor xenografts GEO (panel A), DLD-1 panel B), or HT-29 (panel C), treated by intraperitoneal injection with saline or IMC-11F8 twice a week at 0.3 mg or 1.0 mg/injection, alone or in combination with CPT-11 at the dose of 100 mg/kg once a week. Tumor sizes were measured twice a week. Data represent the mean ± SE of tumor measurements from 10 animals in each group. (D) Tumor regression upon treatment with IMC-11F8 alone or in combination with CPT-11. Each treatment group consists 10 tumor-bearing animals.
Figure 14:
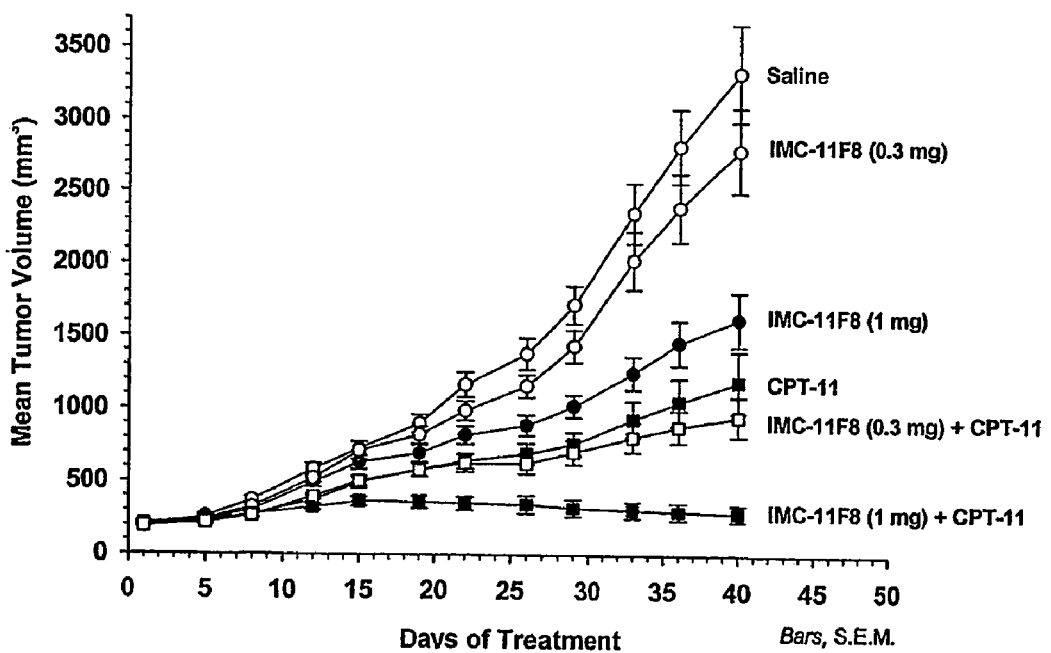
Figure 14:
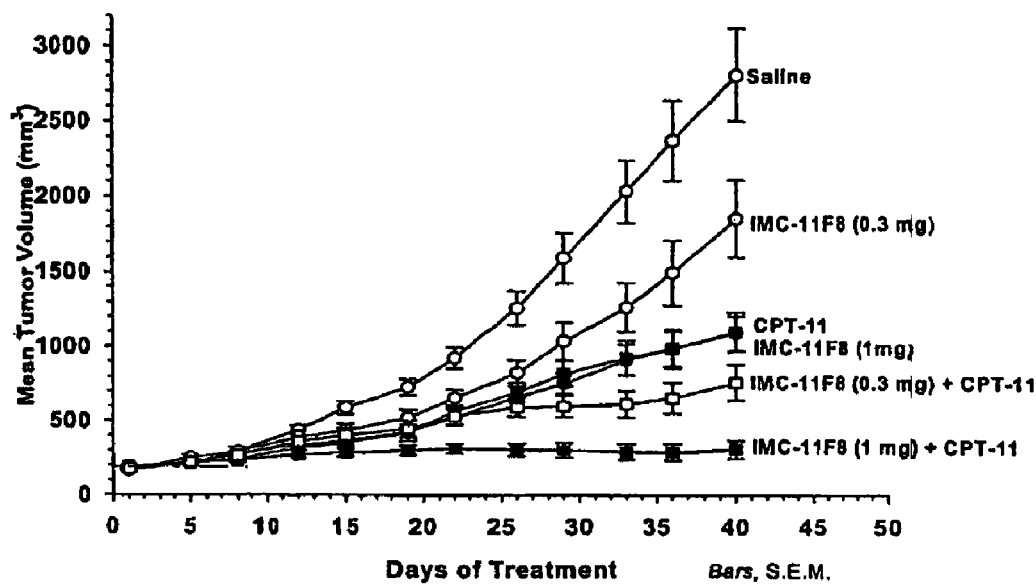
Figure 14:
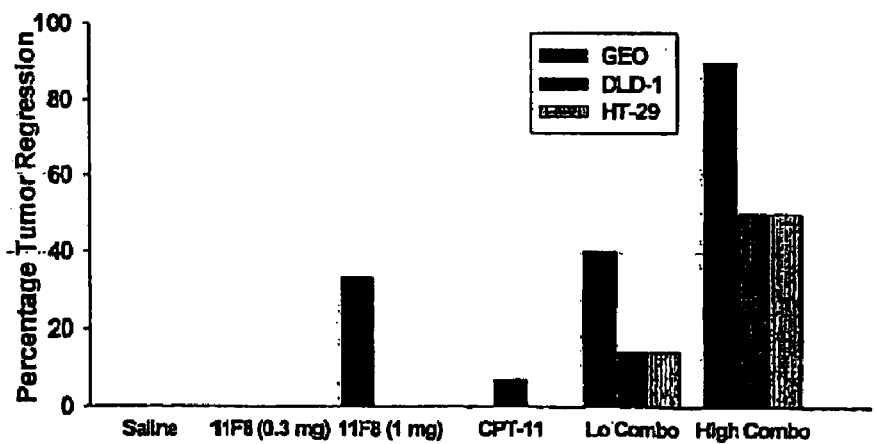

Treatment with IMC-11F8 at either 0.3 mg or 1.0 mg/mouse/injection significantly inhibited the growth of all three colorectal xenografts (GEO, DLD-1, or HT-29; FIG. 14A-C). When administered to mice bearing GEO xenografts in combination with CPT-11, IMC-11F8 significantly increased the tumor growth inhibition observed with CPT-11 alone (FIG. 14A; p<0.01 for both doses of IMC-11F8). Moreover while CPT-11 alone caused no tumor regressions in this model, 4 out of 10 and 9 out of 10 tumor regressions were achieved when CPT-11 was combined with IMC-11F8 at 0.3 mg or 1.0 mg/mouse/injection, respectively (p=0.004 and p<0.0001, respectively). Similar combinational anti-tumor effects were observed in two other xenografts, DLD-1 (FIG. 14B) and HT-29 (FIG. 14C) with equivalent statistical significance in tumor regression in the higher antibody dose (1.0 mg) group. FIG. 14D illustrates the significant increase in the number of tumor regressions observed when CPT-11 is combined with 1MC-11F8 in these three colorectal carcinoma xenografts models.

Example 13

Pharmacokinetics of IMC-11F8

The pharmacokinetics of IMC-11 F8 was studied in cynomolgus monkeys and compared to the pharmacokinetics of IMC-C225. A single dose pharmacokinetic study at 20.5 mg/kg $^{125}$I-radio-labeled IMC-11F8 and IMC-C225 was separately injected intravenously in monkey and blood was drawn at day to determine the level of antibody that is retained in the plasma of the animal. Table 6 provides a pharmacokinetics comparison of IMC-11F8 and IMC-C225 in cynomolgus monkeys.

TABLE 6

|  | IMC-11F8 | IMC-C225 |
| --- | --- | --- |
| $C_{max}$ (mg/L) | 1213 | 1161 |
| $T_{max}$ (hrs) | 0.75 | 0.117 |
| $T_{1/2}$ (hrs) | 116 | 117 |
| AUC (mg*hr/L) | 115400 | 97871 |
| CI (mL/hr) | 0.736 | 0.636 |

It is understood and expected that variations in the principles of invention herein disclosed may be made by one skilled in the art and it is intended that such modifications are to be included within the scope of the present invention.

What is claimed is:

1. An isolated antibody or antibody thereof, comprising at CDRH1 the amino acid sequence: SGDYYWS (SEQ ID NO:2); at CDRH2 the amino acid sequence: YIYYSGSTDYNPSLKS (SEQ ID NO:4) and at CDRH3 the amino acid sequence: VSIFGVGTFDY (SEQ ID NO:6) and at CDRL1 the amino acid sequence: RASQSVSSYLA (SEQ ID NO:10); at CDRL2 the amino acid sequence: DASNRAT (SEQ ID NO: 12); and at CDRL3 the amino acid sequence: HQYGSTPLT (SEQ ID NO: 14), wherein the antibody or fragment thereof binds to EGFR.

2. The antibody or antibody fragment of claim 1, which comprises SEQ ID NO:8.

3. The antibody or antibody fragment of claim 1, which comprises SEQ ID NO:16.

4. The antibody or antibody fragment of claim 1, which comprises SEQ ID NO:8 and SEQ ID NO:16.

* * * * *

UNITED STATES PATENT AND TRADEMARK OFFICE
CERTIFICATE OF CORRECTION

| | | |
|---|---|---|
| PATENT NO. | : 7,598,350 B2 | |
| APPLICATION NO. | : 10/593804 | |
| DATED | : October 6, 2009 | |
| INVENTOR(S) | : Meilin Liu and Zhenping Zhu | |

It is certified that error appears in the above-identified patent and that said Letters Patent is hereby corrected as shown below:

Column 1, line 5, delete "60/544,555" and insert --60/554,555--, therefor.

Column 1, line 6, delete "60/624,624" and insert --60/624,264--, therefor.

Signed and Sealed this
Tenth Day of July, 2012

David J. Kappos
*Director of the United States Patent and Trademark Office*

UNITED STATES PATENT AND TRADEMARK OFFICE
CERTIFICATE OF CORRECTION

PATENT NO.       : 7,598,350 B2                                       Page 1 of 1
APPLICATION NO.  : 10/593804
DATED            : October 6, 2009
INVENTOR(S)      : Meilin Liu et al.

It is certified that error appears in the above-identified patent and that said Letters Patent is hereby corrected as shown below:

Column 39, Claim 1, line 1, insert --fragment-- after "1. An isolated antibody or antibody..."

Signed and Sealed this
Twenty-third Day of February, 2016

Michelle K. Lee
*Director of the United States Patent and Trademark Office*

SEQUENCE LISTING

```
<160> NUMBER OF SEQ ID NOS: 25

<210> SEQ ID NO 1
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 1 agt ggt gat tac tac tgg agt                                          21
Ser Gly Asp Tyr Tyr Trp Ser
 1               5
```

<210> SEQ ID NO 2
<211> LENGTH: 7
<212> TYPE: PRT
<213> ORGANISM: Homo sapiens

<400> SEQUENCE: 2

Ser Gly Asp Tyr Tyr Trp Ser
 1               5

<210> SEQ ID NO 3
<211> LENGTH: 48
<212> TYPE: DNA
<213> ORGANISM: Homo sapiens
<220> FEATURE:
<221> NAME/KEY: CDS
<222> LOCATION: (1)..(48)

<400> SEQUENCE: 3 tac atc tat tac agt ggg agc acc gac tac aac ccg tcc ctc aag agt     48
Tyr Ile Tyr Tyr Ser Gly Ser Thr Asp Tyr Asn Pro Ser Leu Lys Ser
 1               5                  10                  15

<210> SEQ ID NO 4
<211> LENGTH: 16
<212> TYPE: PRT
<213> ORGANISM: Homo sapiens

<400> SEQUENCE: 4

Tyr Ile Tyr Tyr Ser Gly Ser Thr Asp Tyr Asn Pro Ser Leu Lys Ser
 1               5                  10                  15

<210> SEQ ID NO 5
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 5 gtg tcg att ttt gga gtg ggg aca ttt gac tac                         33
Val Ser Ile Phe Gly Val Gly Thr Phe Asp Tyr
 1               5                  10

<210> SEQ ID NO 6
<211> LENGTH: 11
<212> TYPE: PRT
<213> ORGANISM: Homo sapiens

<400> SEQUENCE: 6

Val Ser Ile Phe Gly Val Gly Thr Phe Asp Tyr
 1               5                  10

<210> SEQ ID NO 7
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 7 cag gtg cag ctg cag gag tcg ggc cca gga ctg gtg aag cct tca cag     48
Gln Val Gln Leu Gln Glu Ser Gly Pro Gly Leu Val Lys Pro Ser Gln
 1               5                  10                  15

```
acc ctg tcc ctc acc tgc act gtc tct ggt ggc tcc atc agc agt ggt        96
Thr Leu Ser Leu Thr Cys Thr Val Ser Gly Gly Ser Ile Ser Ser Gly
            20                  25                  30 gat tac tac tgg agt tgg atc cgc cag ccc cca ggg aag ggc ctg gag       144
Asp Tyr Tyr Trp Ser Trp Ile Arg Gln Pro Pro Gly Lys Gly Leu Glu
        35                  40                  45 tgg att ggg tac atc tat tac agt ggg agc acc gac tac aac ccg tcc       192
Trp Ile Gly Tyr Ile Tyr Tyr Ser Gly Ser Thr Asp Tyr Asn Pro Ser
    50                  55                  60 ctc aag agt cga gtc acc atg tcc gta gac acg tcc aag aat cag ttt       240
Leu Lys Ser Arg Val Thr Met Ser Val Asp Thr Ser Lys Asn Gln Phe
65                  70                  75                  80 tcc ctg aag gtc aac tct gtg acc gcc gca gac acg gct gtg tat tac       288
Ser Leu Lys Val Asn Ser Val Thr Ala Ala Asp Thr Ala Val Tyr Tyr
                85                  90                  95 tgt gcg aga gtg tcg att ttt gga gtg ggg aca ttt gac tac tgg ggc       336
Cys Ala Arg Val Ser Ile Phe Gly Val Gly Thr Phe Asp Tyr Trp Gly
            100                 105                 110 cag ggc acc ctg gtc acc gtc tca agc                                   363
Gln Gly Thr Leu Val Thr Val Ser Ser
        115                 120

<210> SEQ ID NO 8
<211> LENGTH: 121
<212> TYPE: PRT
<213> ORGANISM: Homo sapiens

<400> SEQUENCE: 8

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser
        115                 120

<210> SEQ ID NO 9
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 9 agg gcc agt cag agt gtt agc agc tac tta gcc                            33
Arg Ala Ser Gln Ser Val Ser Ser Tyr Leu Ala
 1               5                  10

<210> SEQ ID NO 10
<211> LENGTH: 11
<212> TYPE: PRT
```

<210> ORGANISM: Homo sapiens

<400> SEQUENCE: 10

Arg Ala Ser Gln Ser Val Ser Ser Tyr Leu Ala
 1               5                  10

<210> SEQ ID NO 11
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 11 gat gca tcc aac agg gcc act                                          21
Asp Ala Ser Asn Arg Ala Thr
 1               5

<210> SEQ ID NO 12
<211> LENGTH: 7
<212> TYPE: PRT
<213> ORGANISM: Homo sapiens

<400> SEQUENCE: 12

Asp Ala Ser Asn Arg Ala Thr
 1               5

<210> SEQ ID NO 13
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 13 cac cag tat ggt agc aca cct ctc act                                  27
His Gln Tyr Gly Ser Thr Pro Leu Thr
 1               5

<210> SEQ ID NO 14
<211> LENGTH: 9
<212> TYPE: PRT
<213> ORGANISM: Homo sapiens

<400> SEQUENCE: 14

His Gln Tyr Gly Ser Thr Pro Leu Thr
 1               5

<210> SEQ ID NO 15
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 15 gaa att gtg atg aca cag tct cca gcc acc ctg tct ttg tct cca ggg      48
Glu Ile Val Met Thr Gln Ser Pro Ala Thr Leu Ser Leu Ser Pro Gly
 1               5                  10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc     144

-continued

```
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc      192
Tyr Asp Ala Ser Asn Arg Ala Thr Gly Ile Pro Ala Arg Phe Ser Gly
 50                  55                  60 agt ggg tct ggg aca gac ttc act ctc acc atc agc agc cta gag cct      240
Ser Gly Ser Gly Thr Asp Phe Thr Leu Thr Ile Ser Ser Leu Glu Pro
 65                  70                  75                  80 gaa gat ttt gca gtg tat tac tgt cac cag tat ggt agc aca cct ctc      288
Glu Asp Phe Ala Val Tyr Tyr Cys His Gln Tyr Gly Ser Thr Pro Leu
                 85                  90                  95 act ttc ggc gga ggg acc aag gcg gag atc aaa                          321
Thr Phe Gly Gly Gly Thr Lys Ala Glu Ile Lys
            100                 105

<210> SEQ ID NO 16
<211> LENGTH: 107
<212> TYPE: PRT
<213> ORGANISM: Homo sapiens

<400> SEQUENCE: 16

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Tyr Gly Ser Thr Pro Leu
                 85                  90                  95

Thr Phe Gly Gly Gly Thr Lys Ala Glu Ile Lys
            100                 105

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 17

Gly Gly Gly Gly Ser Gly Gly Gly Gly Ser
 1               5                  10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 18

Gly Gly Gly Gly Ser
 1               5

<210> SEQ ID NO 19
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 19

Gly Gly Gly Gly Ser Gly Gly Gly Gly Ser Gly Gly Gly Gly Ser
 1               5                  10                  15

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20 tccttttct agtagcaact gcaactggag tacattcaca ggtgcagctg cagaa         55

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgagctagcg cttgagacgg tgaccagggt g                                  31

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22 tccttttct agtagcaact gcaactggag tacattcaga aattgtgatg acaca         55

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgatctagaa ctcacgtttg atctccgcct tggtc                              35

<210> SEQ ID NO 24
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gagaagcttg ccgccaccat gggatggtca tgtatcatcc ttttctagt agc           53

<210> SEQ ID NO 25
<211> LENGTH: 19
```

-continued

```
<212> TYPE: PRT
<213> ORGANISM: Mus musculus

<400> SEQUENCE: 25

Met Gly Trp Ser Cys Ile Ile Leu Phe Leu Val Ala Thr Ala Thr Gly
 1               5                  10                  15

Val His Ser
```